(12) United States Patent
Shimoyama et al.

(10) Patent No.: US 12,370,186 B2
(45) Date of Patent: Jul. 29, 2025

(54) COMBINED PHARMACEUTICAL FORMULATION COMPRISING DRUG-CONTAINING LIPOSOME COMPOSITION AND IMMUNE CHECKPOINT INHIBITOR

(71) Applicant: FUJIFILM Corporation, Tokyo (JP)

(72) Inventors: Susumu Shimoyama, Ashigarakami-gun (JP); Tadaaki Ioroi, Ashigarakami-gun (JP); Mikinaga Mori, Ashigarakami-gun (JP); Tamami Higuchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 765 days.

(21) Appl. No.: 17/125,336

(22) Filed: Dec. 17, 2020

(65) Prior Publication Data

US 2021/0100791 A1 Apr. 8, 2021

Related U.S. Application Data

(63) Continuation of application No. PCT/JP2019/024500, filed on Jun. 20, 2019.

(30) Foreign Application Priority Data

Jun. 20, 2018 (JP) .................. 2018-116707
Nov. 9, 2018 (JP) .................. 2018-211291

(51) Int. Cl.
| | | |
|---|---|---|
| *A61K 31/4745* | (2006.01) | |
| *A61K 9/1271* | (2025.01) | |
| *A61K 31/404* | (2006.01) | |
| *A61K 31/704* | (2006.01) | |
| *A61K 39/395* | (2006.01) | |
| *A61K 47/28* | (2006.01) | |
| *A61P 35/00* | (2006.01) | |

(52) U.S. Cl.
CPC ........ *A61K 31/4745* (2013.01); *A61K 9/1271* (2013.01); *A61K 31/404* (2013.01); *A61K 31/704* (2013.01); *A61K 39/3955* (2013.01); *A61K 47/28* (2013.01); *A61P 35/00* (2018.01)

(58) Field of Classification Search
None
See application file for complete search history.

(56) References Cited

U.S. PATENT DOCUMENTS

| | | |
|---|---|---|
| 5,192,549 A | 3/1993 | Barenolz et al. |
| 5,543,152 A | 8/1996 | Webb et al. |
| 6,355,268 B1 | 3/2002 | Slater et al. |
| 7,060,828 B2 | 6/2006 | Madden et al. |
| 7,811,602 B2 | 10/2010 | Cullis et al. |
| 2004/0022817 A1 | 2/2004 | Tardi et al. |
| 2004/0208935 A1 | 10/2004 | Giovanella et al. |
| 2005/0129753 A1* | 6/2005 | Gabizon ................. A61P 31/00 514/414 |
| 2006/0008909 A1 | 1/2006 | Cullis et al. |
| 2007/0088414 A1 | 4/2007 | Campbell et al. |
| 2007/0116753 A1* | 5/2007 | Hong ..................... A61P 31/04 424/450 |
| 2007/0231379 A1 | 10/2007 | Slater et al. |
| 2008/0075762 A1 | 3/2008 | Tardi et al. |
| 2008/0206139 A1 | 8/2008 | Connor et al. |
| 2009/0217401 A1 | 8/2009 | Korman et al. |
| 2009/0285878 A1 | 11/2009 | Hope et al. |
| 2011/0064794 A1 | 3/2011 | Deng et al. |
| 2011/0159080 A1 | 6/2011 | Lowery |
| 2011/0274625 A1 | 11/2011 | Redelmeier et al. |
| 2012/0058178 A1 | 3/2012 | Kikuchi et al. |
| 2013/0052259 A1 | 2/2013 | Barenholz et al. |
| 2013/0202686 A1 | 8/2013 | Yamashita et al. |
| 2015/0030672 A1 | 1/2015 | Li et al. |
| 2015/0258085 A1 | 9/2015 | Bankiewicz |
| 2016/0194625 A1 | 7/2016 | Hoge et al. |
| 2017/0020816 A1 | 1/2017 | Nagy et al. |

(Continued)

FOREIGN PATENT DOCUMENTS

| | | |
|---|---|---|
| CA | 2 582 242 A1 | 4/2006 |
| CA | 2 566 559 C | 5/2014 |

(Continued)

OTHER PUBLICATIONS

Zucker et al (JCR, 160, 2012, 281-289) (Year: 2012).*
Office Action issued Apr. 26, 2022 in Chinese Application No. 201980040973.9.
Notice of Allowance issued Mar. 16, 2022 in U.S. Appl. No. 16/583,518.
Office Action dated Mar. 22, 2023 in Chinese Application No. 201980064960.5, corresponding to U.S. Appl. No. 17/219,064.
Office Action dated Apr. 26, 2023 in Chinese Application No. 202111595172.4, corresponding to U.S. Appl. No. 17/882,144.
Extended European Search Report dated Aug. 17, 2021 in European Application No. 19869479.6, corresponding to U.S. Appl. No. 17/219,064.
Yasuyuki Sadzuka et al., "Effect of Polyethyleneglycol (PEG) Chain on Cell Uptake of PEG-Modified Liposomes", Journal of Liposome Research, 2003, vol. 13, No. 2, pp. 157-172 (16 pages total).

(Continued)

*Primary Examiner* — Celeste A Roney
(74) *Attorney, Agent, or Firm* — Sughrue Mion, PLLC

(57) ABSTRACT

An object of the present invention is to provide a pharmaceutical formulation obtained by combining a liposome composition in which liposomes encapsulate a drug with an immune checkpoint inhibitor. According to the present invention, there is provided a pharmaceutical formulation including (A) a liposome composition in combination with (B) an immune checkpoint inhibitor, in which the liposome composition includes, as constitutional components of a liposome membrane, a hydrophilic polymer-modified diacylphosphatidylethanolamine; a dihydrosphingomyelin, and cholesterols, the liposome composition includes a drug and has art inner water phase containing ammonium sulfate, a molar ratio of sulfate ions in the inner water phase to the drug in an entire water phase is 0.36 or more, and the liposome composition and the immune checkpoint inhibitor are administered simultaneously or sequentially.

16 Claims, 5 Drawing Sheets

(56) References Cited

U.S. PATENT DOCUMENTS

| | | | |
|---|---|---|---|
| 2017/0209574 A1* | 7/2017 | Cao | G01N 33/574 |
| 2017/0282144 A1 | 10/2017 | Sugiyama et al. | |
| 2018/0243214 A1 | 8/2018 | Kitahashi et al. | |
| 2019/0314335 A1 | 10/2019 | Yoshino et al. | |
| 2020/0016079 A1 | 1/2020 | Kasagi et al. | |
| 2021/0038518 A1 | 2/2021 | Kasagi et al. | |
| 2021/0213051 A1 | 7/2021 | Okada et al. | |
| 2022/0370352 A1 | 11/2022 | Kasagi et al. | |

FOREIGN PATENT DOCUMENTS

| | | | |
|---|---|---|---|
| CN | 102764234 A | 11/2012 | |
| CN | 104771361 A | 7/2015 | |
| EP | 0 361 894 A2 | 4/1990 | |
| EP | 1 750 673 B1 | 12/2009 | |
| JP | 02-196713 A | 8/1990 | |
| JP | 2659136 B2 | 9/1997 | |
| JP | 2006-340714 A | 12/2006 | |
| JP | 2008-519045 A | 6/2008 | |
| JP | 2016-117005 A | 6/2016 | |
| JP | 2017-512840 A | 5/2017 | |
| JP | 2020-158542 A | 10/2020 | |
| WO | 2005/120461 * | 12/2005 | |
| WO | WO-2005120461 A2 * | 12/2005 | A61K 31/4745 |
| WO | 2006/121168 A1 | 11/2006 | |
| WO | 2010/113984 A1 | 10/2010 | |
| WO | 2012/091054 A1 | 7/2012 | |
| WO | 2013/059922 A1 | 5/2013 | |
| WO | 2017/069291 * | 4/2017 | |
| WO | 2017/078008 A1 | 5/2017 | |
| WO | 2017/079303 A1 | 5/2017 | |
| WO | 2018/083470 A1 | 5/2018 | |
| WO | 2018/106729 A1 | 6/2018 | |
| WO | 2018/124033 A1 | 7/2018 | |
| WO | 2018/181963 A1 | 10/2018 | |

OTHER PUBLICATIONS

Office Action dated Mar. 25, 2023 in Taiwanese Application 108135454, corresponding to U.S. Appl. No. 17/219,064.
Office Action dated Jun. 23, 2021 from the Brazilian Patent Office in Application No. BR112019020406-7, corresponding to U.S. Appl. No. 16/583,518.
Office Action dated Nov. 30, 2022 issued by the Chinese Patent Office in Chinese Application No. 202111595172.4 corresponding to U.S. Appl. No. 17/882,144.
Office Action dated Nov. 28, 2022 issued by the Chinese Patent Office in Chinese Application No. 201980064960.5 corresponding to U.S. Appl. No. 17/219,064.
Office Action dated Jan. 6, 2023 issued by the Taiwanese Patent Office in Taiwanese Application No. 108135454 corresponding to U.S. Appl. No. 17/219,064.
Office Action dated Jan. 17, 2023 issued by the Japanese Patent Office in Japanese Application No. 2022-005193 corresponding to U.S. Appl. No. 17/882,144.
Jianguo Ma et al., "Synergistic cytotoxicity of cisplatin and topotecan or SN-38 in a panel of eight solid-tumor cell lines in vitro", Cancer Chemother Pharmacol, 1998, vol. 41, pp. 307-316 (10 pages total).
Leilei Xu, "Preparation and ex vivo evaluation of topotecan hydrochloride liposomes", Wanfang, 2014, pp. 27, 30, and 32-33 (7 pages total).
Michael J.W. Johnston et al., "Characterization of the drug retention and pharmacokinetic properties of liposomal nanoparticles containing dihydrosphingomyelin", Biochimica et Biophysica Acta, 2007, vol. 1768, pp. 1121-1127 (7 pages total).
Bai Xiuping et al., "Experts face to face with you on Ovarian Sugamo Cancer", China Pharmaceutical Technology Publishing Co., 2015 (4 pages total).
Office Action dated Dec. 14, 2023, issued in U.S. Appl. No. 17/219,064.

Office Action dated Jun. 27, 2023 from the Chinese Patent Office in Application No. 201880023073.9.
International Preliminary Report on Patentability with translation of Written Opinion for PCT/JP2019/038708 dated Mar. 23, 2021, corresponding to U.S. Appl. No. 17/219,064.
International Search Report for PCT/JP2019/038708 dated Dec. 10, 2019 [PCT/ISA/210], corresponding to U.S. Appl. No. 17/219,064.
Office Action issued May 11, 2021 in U.S. Appl. No. 16/583,518.
Written Opinion of the International Searching Authority for PCT/JP2019/038708 dated Dec. 10, 2019 [PCT/ISA/237], corresponding to U.S. Appl. No. 17/219,064.
Zeghari-Squalli et al., "Cellular Pharmacology of the Combination of the DNA Topoisomerase I Inhibitor SN-38 and the Diaminocyclohexane Platinum Derivative Oxaliplatin", Clinical Cancer Research, May 1999, vol. 5, pp. 1189-1196 (9 pages total).
U.S. Appl. No. 17/219,064, filed Mar. 31, 2021 (Okada et al.).
Non-Final Office Action issued Feb. 7, 2022 in co-pending U.S. Appl. No. 17/079,759.
Office Action dated Mar. 1, 2022 from the Japanese Patent Office in Japanese Application No. 2020-550444.
U.S. Appl. No. 16/583,518, filed Sep. 26, 2019 (Kasagi).
U.S. Appl. No. 17/079,759, filed Oct. 26, 2020 (Kasagi).
Office Action dated Aug. 29, 2023 from the Taiwan Patent Office in Taiwan Application No. 108121444.
Communication issued Sep. 10, 2021 from the China National Intellectual Property Administration in Chinese Application No. 201880023073.9, corresponds to U.S. Appl. No. 16/583,518.
Notice of Reasons for Refusal issued Nov. 9, 2021 from the Japanese Patent Office in Japanese Application No. 2020-525795, corresponds to U.S. Appl. No. 16/583,518.
Communication dated Jun. 22, 2022 from the Chinese Patent Office in Chinese Application No. 201980064960.5, corresponding to U.S. Appl. No. 17/219,064.
Xu Leilei et al., "Preparation and Pharmacokinetics in Rats of Topotecan Hydrochloride Liposomes by. Ammonium Sulfate Gradient Method", Chinese Journal of Pharmaceuticals, 2014, vol. 45, No. 12, pp. 1139-1142 (4 pages total).
Office Action issued Oct. 27, 2022 in Chinese Application No. 201980040973.9, corresponds to U.S. Appl. No. 17/125,336.
European Office Action dated Mar. 2, 2023 in corresponding European Application No. 19823228.2.
Office Action issued Nov. 17, 2023 in Chinese Application No. 201880023073.9, corresponding to U.S. Appl. No. 17/882,144.
Silverman et al., "In vitro experiments showing enhanced release of doxorubicin from Doxil® in the presence of ammonia may explain drug release at tumor site", Nanomedicine: Nanotechnology, Biology, and Medicine, vol. 11, 2015, pp. 1841-1850 (14 pages total).
Fugit et al., "Ion-Pairing Contribution to the Liposomal Transport of Topotecan as Revealed by Mechanistic Modeling", Journal of Pharmaceutical Sciences, vol. 106, 2017, pp. 1149-1161.
International Search Report for PCT/JP2019/024500 dated Aug. 27, 2019 PCT/ISA/210, corresponding to U.S. Appl. No. 17/125,336 (the present application).
Written Opinion for PCT/JP2019/024500 dated Aug. 27, 2019 PCT/ISA/210, corresponding to U.S. Appl. No. 17/125,336 (the present application).
International Preliminary Report on Patentability with English Translation of Written Opinion of the International Searching Authority for PCT/JP2019/024500 dated Dec. 22, 2020, corresponding to U.S. Appl. No. 17/125,336 (the present application).
Office Action issued Jan. 10, 2020 in U.S. Appl. No. 16/583,518.
Office Action issued Jul. 24, 2020 in U.S. Appl. No. 16/583,518.
William C. Zamboni et al., "A Pharmacokinetic Study of a Novel Sphingomyelin/Cholesterol Liposomal Topotecan and Non-Liposomal Topotecan in Rats", AACR-NCI-EORTC International Conference, San Francisco, California, Oct. 22-26, 2007, #C113, total 1 page.
Michael JOHNSTON et al., "Characterization of the drug retention and pharmacokinetic properties of liposomal nanoparticles containing dihydrosphingomyelin", Biochimica et Biophysica Acta, vol. 1768 2007, pp. 1121-1127 (total 7 pages).
International Search Report for PCT/JP2018/013783 dated May 1, 2018 PCT/ISA/210, corresponding to U.S. Appl. No. 16/583,518.

(56) References Cited

OTHER PUBLICATIONS

Written Opinion for PCT/JP2018/013783 dated May 1, 2018 PCT/ISA/237, corresponding to U.S. Appl. No. 16/583,518.
International Preliminary Report on Patentability with English Translation of Written Opinion of the International Searching Authority for PCT/JP2018/013783 dated Oct. 1, 2019, corresponding to U.S. Appl. No. 16/583,518.
Noble, C., et al., "Characterization of highly stable liposomal and immunolipsomal formulations of vincristine and vinblastine", Cancer Chemotherapy and Pharmacology, 2009, vol. 64, No. 4, pp. 741-751.
Extended European Search Report dated Feb. 24, 2020 from the European Patent Office in European application No. 18776957.5, corresponding to U.S. Appl. No. 16/583,518.
Haran, G., et al., "Transmembrane ammonium sulfate gradients in liposomes produce efficient and stable entrapment of amphipathic weak bases", Biochimica et Biophysica Acta, vol. 1151, No. 2, XP023352276, 1993, pp. 201-215.
Zasadzinski, J., et al., "Novel methods of enhanced retention in and rapid, targeted release from liposomes", Current Opinion in Colloid & Interface Science, vol. 16, No. 3, 2011, pp. 203-214.
Fritze, A. et al., "Remote loading of doxorubicin into liposomes driven by a transmembrane phosphate gradient", Biochimica et Biophysica Acta, vol. 1758, No. 10, 2006, pp. 1633-1640.
Office Action dated Mar. 19, 2020, from the Intellectual Property of India in Indian application No. 201947039515, corresponding to U.S. Appl. No. 16/583,518.
Office Action dated Apr. 28, 2020, from the Australian Patent Office in Australian application No. 2018246024, corresponding to U.S. Appl. No. 16/583,518.
M.L. Immordino et al., "Stealth liposomes: review of the basic science, rationale, and clinical applications, existing and potential", International Journal of Nanomedicine, vol. 1. No. 3, pp. 297-315, 2006 (19 pages total).
Office Action dated Apr. 21, 2020, from the Russian Intellectual Property Office in Russian Application No. 2019130500/04, corresponding to U.S. Appl. No. 16/583,518.
Abraham, Sheela A. et al., "An evaluation of transmembrane ion gradient-mediated encapsulation of topotecan within liposomes", Journal of Controlled Release, vol. 96, Issue 3, May 18, 2004, pp. 449-461, Abstract Only (3 pages total).
Xu Lili, "Preparation and in vitro and in vivo evaluation of topotecan hydrochloride liposomes", Wanfang, Sep. 17, 2014 (88 pages total).
Office Action dated Feb. 26, 2021, from the Intellectual Property of India in Indian application No. 202048031732, a divisional corresponding to U.S. Appl. No. 17/079,759 & U.S. Appl. No. 17/079,759.
Office Action dated Feb. 22, 2021, from the Korean Intellectual Property Office in Korean application No. 10-2019-7028183, corresponding to U.S. Appl. No. 16/583,518.
Office Action dated Mar. 3, 2021, from the China National Intellectual Property Administration in Chinese application No. 201880023073.9, corresponding to U.S. Appl. No. 16/583,518.
Office Action issued Sep. 24, 2021 in U.S. Appl. No. 16/583,518.
Bowen, P., "Particle Size Distribution Measurement from Millimeters to Nanometers and from Rods to Platelets", Journal of Dispersion Science and Technology, 2002, vol. 23, No. 5, pp. 631-662 (33 pages).
Extended European Search Report issued Jul. 1, 2021 in European Application No. 19823228.2.
Office Action dated Mar. 9, 2023 from the Taiwanese Intellectual Property Office in TW Application No. 108121444.
Office Action dated May 13, 2024 in European Application No. 19 869 479.6, corresponding to U.S. Appl. No. 17/219,064.
Office Action issued Mar. 11, 2024 in European Application No. 18 776 957.5, corresponding to U.S. Appl. No. 17/882,144.
Office Action issued Apr. 15, 2024 in U.S. Appl. No. 17/219,064.
U.S. Appl. No. 17/125,336 (the present application), Pending.
U.S. Appl. No. 16/583,518, Pending.
U.S. Appl. No. 17/079,759, Pending.
U.S. Appl. No. 17/219,064, Pending.
Office Action dated Sep. 20, 2024 in U.S. Appl. No. 17/219,064.
Notice of Allowance issued Feb. 3, 2025 in U.S. Appl. No. 17/219,064.
Office Action issued Jan. 28, 2025 in U.S. Appl. No. 17/882,144.
Leilei Xu, Preparation and in Vitro/in Vivo Evaluation of Topotecan Hydrochloride Liposomes, Master's Thesis, Jiangsu University (2014).
Office Action issued in Chinese patent application No. 202310994903.5 dated May 30, 2025, corresponding to U.S. Appl. No. 17/882,144.
Office Action issued Jun. 13, 2025 in Chinese Application No. 202310994904.X; corresponding to U.S. Appl. No. 16.583,518.

* cited by examiner

COMBINED PHARMACEUTICAL FORMULATION COMPRISING DRUG-CONTAINING LIPOSOME COMPOSITION AND IMMUNE CHECKPOINT INHIBITOR

CROSS-REFERENCE TO RELATED APPLICATIONS

This application is a Continuation of PCT International Application No. PCT/JP2019/024500 filed on Jun. 20, 2019, which claims priority under 35 U.S.C. § 119(a) to Japanese Patent Application No. 2018-116707 filed on Jun. 20, 2018 and Japanese Patent Application No. 2018-211291 filed on Nov. 9, 2018. Each of the above application(s) is hereby expressly incorporated by reference, in its entirety, into the present application.

BACKGROUND OF THE INVENTION

1. Field of the Invention

The present invention relates to a pharmaceutical formulation in which a drug-containing liposome composition and an immune checkpoint inhibitor are combined and administered simultaneously or sequentially.

2. Description of the Related Art

In recent years, it has become known that cancer utilizes a system that evades the immune surveillance. Cancer immunotherapy is a therapy that acts on the immune surveillance of cancer patients to strengthen the immunity against cancer, thereby suppressing the progression of cancer or treating cancer. Immune checkpoint molecules such as CTLA-4 and PD-1 or a ligand thereof, PD-L1 are known as molecules used in such an evasion system (WO2006/121168A and JP2006-340714A).

In addition, it is disclosed that co-administration of human anti-PD-1 or an antigen-binding moiety thereof with a chemotherapeutic agent is endowed with two anticancer agents that act by different mechanisms, which have cytotoxic effects on human tumor cells (WO2006/121168A and JP2006-340714A). However, WO2006/121168 A and JP2006-340714A do not disclose an anticancer agent using a liposome in co-administration of human anti-PD-1 or an antigen-binding moiety thereof and a chemotherapeutic agent.

In addition, at the Opdivo Q&A site, in response to the question of whether Opdivo can be used in combination with chemotherapeutic agents, it has been disclosed that Opdivo cannot be used in combination because the efficacy and safety thereof in combination with cancer chemotherapeutic agents have not been established ("ONO ONCOLOGY Opdivo Q&A, Can Opdivo be used in combination with chemotherapeutic agents?", [online], publication date unknown, Ono Pharmaceutical Co., Ltd., [Search on May 2, 2018], Internet <URL: https://www.ono-oncology.jp/contents/patient/opdivo_faq/11.html>).

In chemotherapy, it is often studied that a drug is accumulated at a disease site such as cancer and exposed thereto over a long period of time by means of a liposome composition.

U.S. Pat. No. 7,060,828B2 and [AACR-EORTC International Conference, San Francisco, California, Oct. 22-26, 2007, #C113 A Pharmacokinetics Study of a Novel Sphingomyelin/Cholesterol Liposomal Topotecan and Non-Liposomal Topotecan in Rats, William C. Zamboni et al.] disclose a liposome in which topotecan is encapsulated in a Liposome containing sphingomyelin and cholesterol.

U.S. Pat. No. 7,811,602B2 discloses a liposome in which topotecan is encapsulated in a Liposome containing dihydrosphingomyelin and cholesterol.

JP2008-519045A discloses a liposomal camptothecin preparation adapted to enhance the stability of camptothecin, including (a) camptothecin encapsulated in a liposome, (b) first solution which is external to the liposome and has a pH of 4.5 or less than 4.5, and (c) second solution which is internal to the liposome. It is also disclosed that the liposome contains dihydrosphingomyelin and cholesterol.

JP1990-196713A (JP-H02-196713A) discloses a system for effectively loading an amphiphilic drug into a liposome, including adjusting a liposome suspension in the presence of an ammonium compound or ammonium salt, diluting the suspension with a buffer or salt, and providing an ammonium gradient from the inside to the outside between an inner water phase and an outer water phase and a pH gradient such that the pH of the inside of the liposome is more acidic than the pH of the outside of the liposome.

U.S. Pat. No. 6,355,268B2 discloses a liposome in which topotecan is encapsulated in the presence of ammonium sulfate in a liposome containing purified hydrogenated soybean phospholipid or sphingomyelin, cholesterol, and a hydrophilic polymer derivative lipid.

SUMMARY OF THE INVENTION

The above-mentioned U.S. Pat. Nos. 7,060,828B2, 7,811,602B2, JP2008-519045A, and [AACR-EORTC International Conference, San Francisco, California, Oct. 22-26, 2007, #C113 A Pharmacokinetics Study of a Novel Sphingomyelin/Cholesterol Liposomal Topotecan and Non-Liposomal Topotecan in Rats, William C. Zamboni et al.] disclose that the drug efficacy is improved by encapsulating topotecan in a liposome containing sphingomyelin or dihydrosphingomyelin to suppress the leakage of topotecan in blood and improve the area-under the blood concentration-time curve (AUC). However, since the composition of lipids that constitute the liposome and the composition of salts that precipitate topotecan have not been optimized, the improvement in AUC is not sufficient and therefore further improvement is required for AUC.

An object of the present invention is to provide, in the combination of cancer immunotherapy with an immune checkpoint inhibitor and chemotherapy, a combination of two or more anticancer agents having high therapeutic effects and less side effects by combining two or more anticancer agents that act by different mechanisms.

As a result of extensive studies, the present inventors have found that the foregoing object can be achieved by a pharmaceutical formulation including (A) a liposome composition in combination with (B) an immune checkpoint inhibitor, in which the liposome composition includes, as constitutional components of a liposome membrane, a hydrophilic polymer-modified diacylphosphatidylethanolamine; a dihydrosphingotmyelin; and cholesterols, the liposome composition includes a drug and has an inner water phase containing ammonium sulfate, a molar ratio of sulfate ions in the inner water phase to the drug in an entire water phase is 0.36 or more, and the liposome composition and the immune checkpoint inhibitor are administered simultaneously or sequentially. The present invention has been completed based on these findings.

The present invention provides the following.

[1] A pharmaceutical formulation comprising:
(A) a liposome composition in combination with (B) an immune checkpoint inhibitor,
in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing ammonium sulfate, a molar ratio of sulfate ions in the inner water phase to the drug in an entire water phase is 0.36 or more, and the liposome composition and the immune checkpoint inhibitor are administered simultaneously or sequentially.

[2] The pharmaceutical formulation according to [1], in which the drug is topotecan or a salt thereof, doxorubicin or a salt thereof, irinotecan or a salt thereof, or sunitinib or a salt thereof.

[3] The pharmaceutical formulation according to [1] or [2], in which the molar ratio of sulfate ions in the inner water phase to the drug in the entire water phase is 0.6 or more and 1.8 or less.

[4] The pharmaceutical formulation according to any one of [1] to [3], in which the hydrophilic polymer-modified diacylphosphatidylethanolamine is a polyethylene glycol- or methoxy polyethylene glycol-modified diacylphosphatidyledianolamine,

[5] The pharmaceutical formulation according to any one of [1] to [4], in which a percentage of the hydrophilic polymer-modified diacylphosphatidylethanolamine in the constitutional components of the liposome membrane is 2 to 10 mol %.

[6] The pharmaceutical composition according to any one of [1] to in which a percentage of cholesterols in the constitutional components of the liposome membrane is 35 to 43 mol %.

[7] The pharmaceutical formulation according to any one of [1] to [6], in which a particle size is 150 nm or less.

[8] The pharmaceutical formulation according to any one of [1] to [7], in which an outer water phase has a pH of 5.5 to 8.5.

[9] The pharmaceutical formulation according to any one of [1] to [8], in which the dihydrosphingomyelin is a dihydrosphingomyelin containing a long-chain alkyl group having 16 carbon atoms and a long-chain alkyl group having 18 carbon atoms, and an included drug is topotecan or a salt thereof.

[10] The pharmaceutical formulation according to any one of [1] to [9], in which a drug release rate from a liposome in plasma having an ammonium concentration of 1 mmol/L or less is 20%/24 hours or less at 37° C., and a drug release rate from a liposome in plasma having an ammonium concentration of 4 to 6 mmol/L is 60%/124 hours or more at 37° C.

[11] The pharmaceutical formulation according to any one of [1] to [10], in which the immune checkpoint inhibitor includes at least one selected from a PD-1 inhibitor, a PD-L1 inhibitor, a PD-L2 inhibitor, or a CTLA-4 inhibitor.

[12] The pharmaceutical formulation according to [11], in which the immune checkpoint inhibitor includes at least one selected from a PD-1 inhibitor, a PD-L1 inhibitor, or a CTLA-4 inhibitor.

[13] The pharmaceutical formulation according to any one of [1] to [12], in which the administration is carried out at a dose and for a dosing period that exhibit a therapeutic synergistic effect.

[14] The pharmaceutical formulation according to any one of [1] to [13] in which a subject of administration has resistance to topotecan.

[15] A method for treating a disease (preferably cancer) of a subject, the method comprising:
administering (A) a liposome composition in combination with (B) an immune checkpoint inhibitor to a subject simultaneously or sequentially at an effective dose and for an effective dosing period exhibiting a therapeutic synergistic effect,
in which the liposome composition includes, as constitutional components of a liposorne membrane, a hydrophilic polymer-modified diacylphosphatidylethanolamine; a dihydrosphingomyelin; and cholesterols, the liposome composition includes a drug and has an inner water phase containing ammonium sulfate, and a molar ratio of sulfate ions in the inner water phase to the drug in an entire water phase is 0.36 or more.

[16] A pharmaceutical formulation for use in the treatment of a disease (preferably cancer) of a subject, the pharmaceutical formulation comprising:
(A) a liposome composition in combination with (B) an immune checkpoint inhibitor,
in which the liposome composition includes, as constitutional components of a liposome membrane, a hydrophilic polymer-modified diacylphosphatidylethanolamine; dihydrosphingomyelin; and cholesterols, the liposome composition includes a drug and has an inner water phase containing ammonium sulfate, a molar ratio of sulfate ions in the inner water phase to the drug in an entire water phase is 0.36 or more, and the liposome composition and the immune checkpoint inhibitor are administered simultaneously or sequentially.

[17] Use of a pharmaceutical formulation for the manufacture of a medicine, the pharmaceutical formulation comprising:
(A) a liposome composition in combination with (B) an immune checkpoint inhibitor,
in which the liposome composition includes, as constitutional components of a liposome membrane, a hydrophilic polymer-modified diacylphosphatidylethanolamine, a dihydrosphingomyelin; and cholesterols, the liposome composition includes a drug and has an inner water phase containing ammonium sulfate, a molar ratio of sulfate ions in the inner water phase to the drug in an entire water phase is 0.36 or more, and the liposome composition and the immune checkpoint inhibitor are administered simultaneously or sequentially.

[18] A pharmaceutical formulation comprising:
(A) a liposome composition in combination with (B) an immune checkpoint inhibitor,
in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing an ammonium salt, the dihydrosphingomyelin is a dihydrosphingomyelin containing a long-chain alkyl group having 16 carbon atoms and a long-chain alkyl group having 18 carbon atoms, and the liposome composition and the immune checkpoint inhibitor are administered simultaneously or sequentially.

[19] A pharmaceutical formulation comprising:

(A) a liposome composition in combination with (B) an immune checkpoint inhibitor, in which the liposome composition includes, as constitutional components of a liposome membrane, a hydrophilic polymer-modified diacylphosphatidylethanolamine; dihydrosphingomyelin; and cholesterols, the liposome composition includes a drug, and the liposome composition and the immune checkpoint inhibitor are administered simultaneously or sequentially.

The pharmaceutical formulation according to an aspect of the present invention has at least one effect of treating or preventing cancer by administering a liposome composition and an immune checkpoint inhibitor in combination simultaneously or sequentially.

In addition, the pharmaceutical formulation according to the aspect of the present invention has a high AUC or a long blood half-life, maintains excellent properties of having a strong antitumor activity even in a small amount, and by administering a liposome composition and an immune checkpoint inhibitor in combination simultaneously or sequentially, has a significant and unexpected tumor growth inhibitory effect, which is superior to that in a case where an anticancer agent which is not formulated into a liposome preparation and an immune checkpoint inhibitor are used in combination.

Furthermore, the pharmaceutical formulation according to the aspect of the present invention has a tumor growth inhibitory effect even at a low dose, which enables a desirable treatment that not only has high safety but also low physical burden and high convenience for subjects including patients.

DESCRIPTION OF THE PREFERRED EMBODIMENTS

Figure 1:
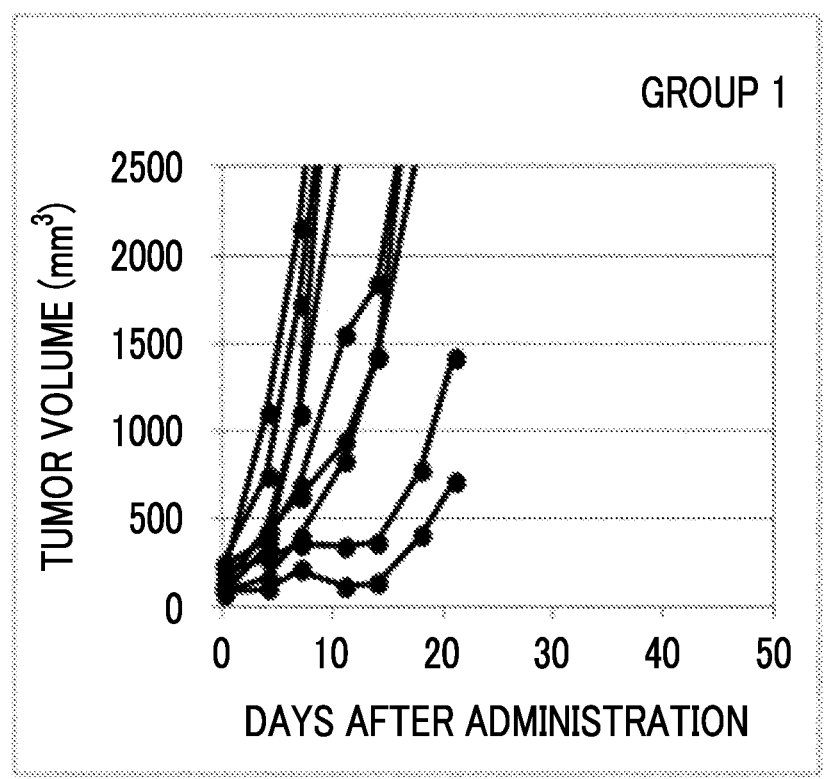
FIG. 1 shows the measurement results of a tumor volume in a drug efficacy test using a tumor-bearing model mouse with subcutaneous transplantation of MBT-2.
Figure 2:
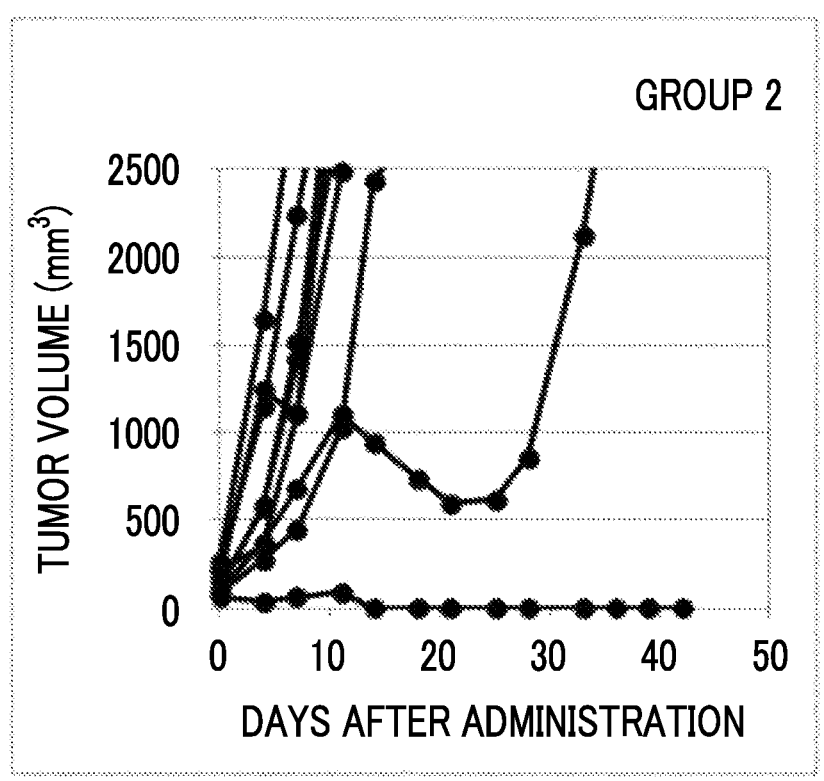
FIG. 2 shows the measurement results of a tumor volume in a drug efficacy test using a tumor-bearing model mouse with subcutaneous transplantation of MBT-2.
Figure 3:
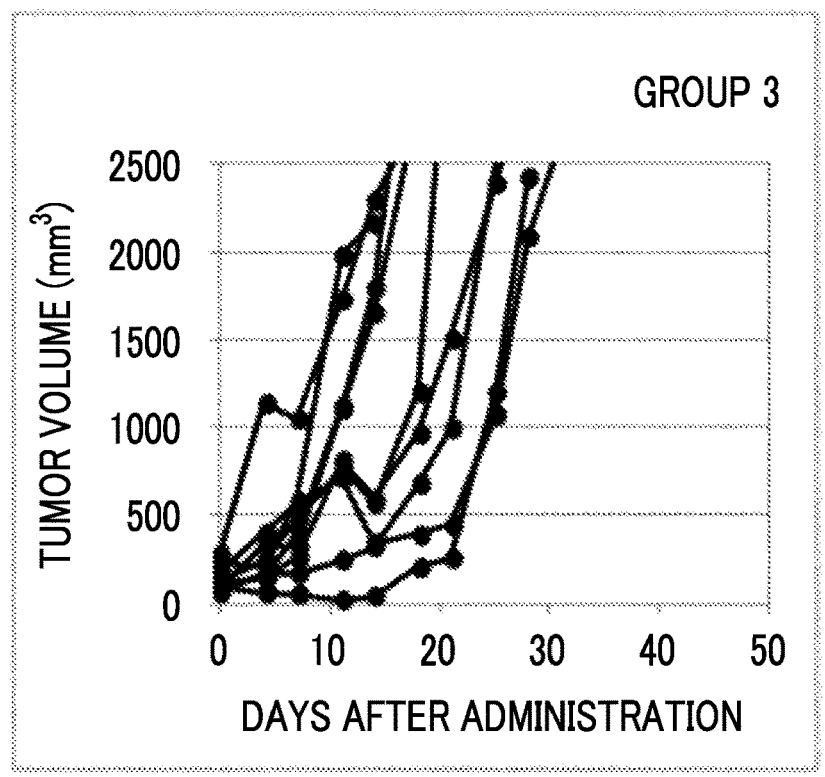
FIG. 3 shows the measurement results of a tumor volume in a drug efficacy test using a tumor-bearing model mouse with subcutaneous transplantation of MBT-2.
Figure 4:
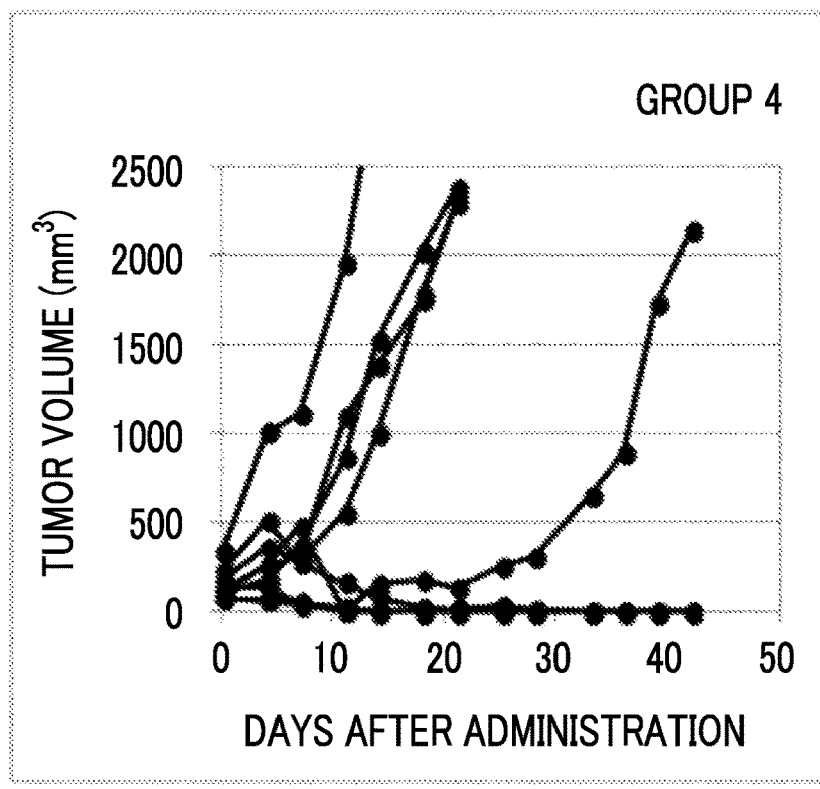
FIG. 4 shows the measurement results of a tumor volume in a drug efficacy test using a tumor-bearing model mouse with subcutaneous transplantation of MBT-2.

Hereinafter, the present invention will be described in detail.

In the present specification, % means mass percentage unless otherwise specified. In the present specification, in a case where a plurality of substances corresponding to components are present in a composition, the amount of each component in the composition means a total amount of the plurality of substances present in the composition, unless otherwise specified.

In the present specification, each term has the following meaning unless otherwise specified.

The term "to" indicates a range including the numerical values described before and after "to" as a minimum value and a maximum value, respectively.

The subject includes humans and mammals other than humans. Examples of mammals other than humans include monkeys, dogs, cats, cows, horses, mice, and rats.

The treatment may be any treatment or therapy that achieves a desired therapeutic effect, for example, inhibition or delay of progression of a condition, and includes slowing down a rate of progression, pausing the rate of progression, improving the condition, healing or remitting the condition (whether partial or complete), preventing, delaying, reducing, or arresting one or a plurality of symptoms and/or signs of the condition, and prolonging subject's survival over that expected in the absence of treatment.

The treatment also includes prevention. For example, treating a subject who is susceptible to or at risk of onset or recurrence of cancer may prevent or delay the onset or recurrence of cancer in the subject.

The treatment may include inhibition of cancer growth including complete remission of cancer, and/or inhibition of cancer metastasis. The cancer growth refers to the transformation of cancer into a more developed form. Examples of an index for measuring the inhibition of cancer growth include decreased survival of cancer cells, decreased tumor volume or morphology (for example, determined using computed tomography (CT), ultrasonography, or other diagnostic imaging methods), delayed tumor growth, destruction of tumor vasculature, improved scores of delayed hypersensitivity skin test, increased activity of cytolytic T-lymphocytes, and decreased levels of tumor-specific antigens.

In the present invention, tumor, malignant tumor, cancer, malignant neoplasm, carcinoma, sarcoma, and the like are collectively referred to as "tumor" or "cancer". In addition, the term "tumor" or "cancer" includes those that have recurred after the treatment of cancer. The term "tumor" includes all malignant or benign neoplastic cell growth and proliferation, as well as pre-cancerous and cancerous cells and tissues.

The term "effective amount" is a dose required to achieve a desired therapeutic or prophylactic result, including the duration and amount of administration. The "effective amount" of the pharmaceutical formulation according to the embodiment of the present invention may vary depending on the disease state, age, sex, and body weight of a subject (or individual), the ability of the pharmaceutical formulation to elicit a desired response in the subject (or individual), and the like.

The term "co-administration" refers to administering a first therapy and a second therapy in a combination therapy at a time interval of about 15 minutes or less, such as any of about 10 minutes, about 5 minutes, or about 1 minute or less. In a case where the first therapy and the second therapy are administered simultaneously, the first therapy and the second therapy can be contained in the same composition (for example, a composition that contains both the first therapy and the second therapy), or can be contained in separate compositions (for example, the first therapy is contained in one composition and the second therapy is contained in another composition).

The term "sequential administration" refers to administering a first therapy and a second therapy in a combination therapy at a time interval of more than about 15 minutes, such as any of about 20 minutes, about 30 minutes, about 40 minutes, about 50 minutes, about 60 minutes or longer day, 2 days, 3 days, 1 week, 2 weeks, 3 weeks, or the like). In the present invention, the sequential administration also includes first administration of the first therapy and first administration of the second therapy. In addition, in the present invention, the sequential administration also includes the administration of the second therapy after the administration of the first therapy (after a predetermined time (for example, after 1 week)). The first therapy and the second therapy may be contained in separate compositions, which may be contained in the same package or kit or may be contained in different packages or kits.

The term "retention in blood" means a property in which a drug in a state of being encapsulated in a liposome is present in blood in a subject to which a liposome composition has been administered.

The "average particle size of liposome" means an average particle size (preferably a cumulant average particle size) measured using a dynamic light scattering method unless otherwise specified. Examples of commercially available determination devices using dynamic light scattering include a concentrated system particle size analyzer SPAR-1000 (manufactured by Otsuka Electronics Co., Ltd.), a Nanotrac UPA (manufactured by Nikkiso Co., Ltd.), and a Nanosizer (manufactured by Malvern Panalytical Ltd.). It is also possible to calculate a volume average particle size and a number average particle size of the liposome by the conversion equation specific to the determination device of each manufacturer. In order to measure particles in the vicinity of 100 nm, the distribution of particles cannot be accurately captured by a static light scattering method or the like, and measurement by the dynamic light scattering method is preferable.

(Pharmaceutical Formulation According to Embodiment of Present Invention)

Hereinafter, the present invention will be described in detail.

The first illustrative embodiment of the pharmaceutical formulation according to the embodiment of the present invention is a pharmaceutical formulation including (A) a liposome composition in combination with (B) an immune checkpoint inhibitor, in which the liposome composition includes, as constitutional components of a liposome membrane, a hydrophilic polymer-modified diacylphosphatidylethanolamine; a dihydrosphingomyelin, and cholesterols, the liposome composition includes a drug and has an inner water phase containing ammonium sulfate, a molar ratio of sulfate ions in the inner water phase to the drug in an entire water phase is 0.36 or more, and the liposome composition and the immune checkpoint inhibitor are administered simultaneously or sequentially.

The second illustrative embodiment of the pharmaceutical formulation according to the embodiment of the present invention is a pharmaceutical formulation including (A) a liposome composition in combination with (B) an immune checkpoint inhibitor, in which the liposome composition includes, as constitutional components of a liposome membrane, a hydrophilic polymer-modified diacylphosphatidylethanolamine: a dihydrosphingomyelin; and cholesterols, the liposome composition includes a drug and has an inner water phase containing an ammonium salt, the dihydrosphingomyelin is a dihydrosphingomyelin containing a long-chain alkyl group having 16 carbon atoms and a long-chain alkyl group having 18 carbon atoms, and the liposome composition and the immune checkpoint inhibitor are administered simultaneously or sequentially.

The third illustrative embodiment of the pharmaceutical formulation according to the embodiment of the present invention is a pharmaceutical formulation including (A) a liposome composition in combination with (B) an immune checkpoint inhibitor, in which the liposome composition includes, as constitutional components of a liposome membrane, a hydrophilic polymer-modified diacylphosphatidylethanolamine; a dihydrosphingomyelin; and cholesterols, the liposome composition includes a drug, and the liposome composition and the immune checkpoint inhibitor are administered simultaneously or sequentially.

The following description relating to the present invention applies to the first to third illustrative embodiments of the pharmaceutical formulation according to the embodiment of the present invention. In addition, the present invention includes aspects resulting from modifications and/or combinations of certain illustrative embodiments of the present invention based on the following description relating to the present invention.

((A) Liposome Composition)

The liposome is a closed vesicular body formed of a lipid bilayer membrane using lipids, and has a water phase (inner water phase) within the space of the closed vesicle. The inner water phase contains water and the like. The liposome is usually present in a state of being dispersed in an aqueous solution (outer water phase) outside a closed vesicular body. In the present invention, the liposome composition refers to a composition including a liposome and an aqueous solution, components, and the like contained outside the liposome. The liposome may be single lamellar (which is also referred to as monolayer lamellar or unilamellar, and is a structure having a single bilayer membrane) or may be multilayered lamellar (which is also referred to as multilamellar and is an onion-like structure having multiple bilayer membranes where individual layers are compartmented by aqueous layers). In the present invention, the liposome is preferably a single lamellar liposome from the viewpoint of safety and stability in pharmaceutical applications. The "encapsulated" means taking a form in which a drug is contained in an inner water phase with respect to the liposome.

The average particle size of the liposome is 10 nm to 1,000 nm, preferably 20 nm to 500 nm, more preferably 30 to 300 nm, still more preferably 30 nm to 200 nm, even more preferably 150 nm or less, for example, 30 nm to 150 nm, and particularly preferably 70 to 150 nm. The liposome preferably has a spherical shape or a shape close thereto.

In a case where an enhanced permeability and retention effect (EPR effect) is expected, the size (average particle size) of the liposome is preferably substantially 50 to 200 nm in diameter, more preferably substantially 50 to 150 nm in diameter, and still more preferably substantially 50 to 100 nm in diameter. The term "substantially" means that at least 75% of the number of liposomes are within a specified diameter range. The "at least 75%" is more preferably at least 80% and still more preferably at least 90%.

The component (membrane component) that constitutes the lipid bilayer of the liposome includes a lipid. Any lipid soluble in a mixed solvent of a water-soluble organic solvent and an ester-based organic solvent can be used as the lipid. Specific examples of the lipid include a phospholipid, a lipid other than phospholipid, cholesterols, and derivatives thereof. These components may be constituted of a single component or a plurality of components. The liposome in the present invention includes a hydrophilic polymer-modi- 16 carbon atoms and a long-chain alkyl group having 20 to 24 carbon atoms.

From the viewpoint of preventing leakage of a drug from the liposome, the following compound having a long-chain alkyl group having 16 carbon atoms and a long-chain alkyl group having 18 carbon atoms is preferably used as the dihydrosphingomyelin. This is because the melting point becomes higher as the number of carbon atoms is larger, and therefore a liposome membrane having high partition properties can be formed.

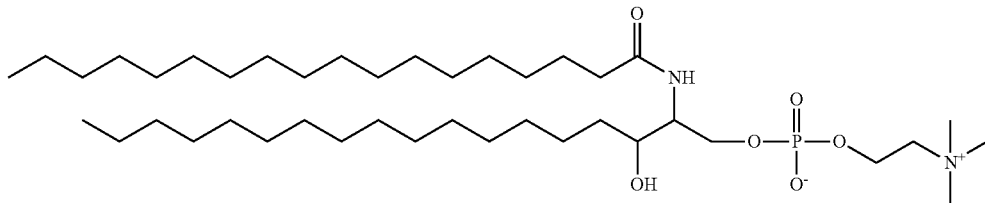

fied diacylphosphatidylethanolamine, dihydrosphingomyelin, and cholesterols as the constitutional components of the liposome membrane.

Examples of the lipid serving as a base material for forming a lipid bilayer membrane include a phospholipid having two acyl chains, for example, a natural or synthetic phospholipid such as phosphatidylcholine (lecithin), phosphatidyl glycerol, phosphatidic acid, phosphatidylcholine, phosphatidyl ethanolamine, phosphatidyl serine, phosphatidyl inositol, sphingomyelin, or cardiolipin, and a hydrogenated product thereof (for example, hydrogenated soy phosphatidylcholine (HSPC)).

In the present invention, dihydrosphingomyelin, which is a phospholipid having two acyl chains, is used as a lipid serving as a base material for forming a lipid bilayer membrane. The retention of liposomes in blood can be improved by using dihydrosphingomyelin.

By using dihydrosphingomyelin as a base material of the liposome membrane, the partition properties of the liposome membrane can be improved and therefore the leakage of the encapsulated drug can be prevented. It is speculated that this is because amide bonds of dihydrosphingomyelin have strong hydrogen bonding ability and can form a strong and highly partitionable membrane by strongly interacting with each other. In addition, amide bonds of dihydrosphingomyelin strongly interact with hydroxyl groups of cholesterol used simultaneously in the present invention, whereby a membrane having high partition properties can be formed. This is a function that cannot be achieved with commonly used lipids such as HSPC and lecithin having ester bonds.

In addition, since completely saturated dihydrosphingomyelin has a higher melting point and a lower mobility of the formed membrane relative to sphingomyelin having amide bonds but having unsaturated bonds in the acyl chain, it is speculated that dihydrosphingomyelin can form a membrane with higher partition properties relative to sphingomyelin.

Dihydrosphingomyelin generally has two long-chain alkyl groups in the molecule and examples of the dihydrosphingomyelin having two long-chain alkyl groups include dihydrosphingomyelin having two long-chain alkyl groups having 16 carbon atoms, dihydrosphingomyelin having a long-chain alkyl group having 16 carbon atoms and a long-chain alkyl group having 18 carbon atoms, and dihydrosphingomyelin having a long-chain alkyl group having As dihydrosphingomyelin, for example, dihydrosphingomyelin obtained by reducing naturally occurring sphingomyelin by a general method may be used, or dihydrosphingomyelin obtained by synthesis may be used. Since most dihydrosphingomyelins derived from natural products such as chicken eggs generally have two long-chain alkyl groups having 16 carbon atoms, it is preferable to use dihydrosphingomyelin obtained by chemical synthesis, from the viewpoint that. dihydrosphingomyelin having a long-chain alkyl group having 16 carbon atoms and a long-chain alkyl group having 18 carbon atoms can be obtained with high purity.

The percentage of dihydrosphingomyelin in the constitutional components of the liposome membrane (the total lipids constituting the liposome) is preferably 30 to 80 mol %, more preferably 40 to 70 mol %, and still more preferably 50 to 60 mol %.

Examples of the hydrophilic polymer in the hydrophilic polymer-modified diacylphosphatidylethanolamine include polyethylene glycols, polyglycerins, polypropylene glycols, polyvinyl alcohols, styrene-maleic acid anhydride alternating copolymers, polyvinylpyrrolidones, and synthetic polyamine acids. The hydrophilic polymers may be used alone or in combination of two or more thereof.

Among these, from the viewpoint of retention in blood of a composition, polyethylene glycols, polyglycerins, and polypropylene glycols are preferable, and polyethylene glycol (PEG), polyglycerin (PG), polypropylene glycol (PPG), and derivatives thereof are more preferable.

Polyethylene glycol (PEG) and derivatives thereof are still more preferable from the viewpoint of versatility and retention in blood. Examples of derivatives of polyethylene glycol (PEG) include, but are not particularly limited to, methoxy polyethylene glycols.

The molecular weight of polyethylene glycols is not particularly limited and is 500 to 10,000 daltons, preferably 1,000 to 7,000 daltons, and more preferably 2,000 to 5,000 daltons.

The number of carbon atoms in the acyl moiety of diacylphosphatidylethanolamine is preferably 16 or more, for example, preferably 16 or more and 30 or less, more preferably 16 or more and 24 or less, and still more preferably 20.

Examples of the polyethylene glycol-modified diacylphosphatidylethanolamine include 1,2-distearoyl-3-phosphatidylethanolamine-polyethylene glycols such as 1,2- distearoyl-3-phosphatidylethanolamine-PEG2000 (manufactured by Nippon Oil & Fats Co., Ltd.), 1,2-distearoyl-3-phosphatidylethanolamine-PEG5000 (manufactured by Nippon Oil & Fats Co., Ltd.), and distearoyl glycerol-PEG2000 (manufactured by Nippon Oil & Fats Co., Ltd.).

The percentage of the hydrophilic polymer-modified diacylphosphatidylethanolamine in the constitutional components of the liposome membrane (the total lipids constituting the liposome) is preferably 1 to 15 mol % and more preferably 2. to 10 mol %.

Examples of cholesterols include cholesterols which contain cyclopentahydrophenanthrene as a basic skeleton and in which carbon atoms are partially or completely hydrogenated and derivatives thereof. For example, cholesterol is preferable. In a case where the average particle size of the liposome decreases to 100 nm or less, the curvature of the lipid membrane becomes higher. The deformation of the membrane arranged in the liposome also becomes larger. It is effective to add cholesterol or the like in order to fill the deformation of the membrane caused by lipid (membrane-stabilizing effect).

In connection with the liposome, the addition of cholesterol is expected to lower the fluidity of the membrane of the liposome, for example, by filling the gaps in the membrane of the liposome.

The percentage of cholesterol in the constitutional components of the liposome membrane (lipids constituting the liposome) is preferably 20 mol % to 50 mol %, more preferably 30 mol % to 45 mol %, and still more preferably 35 mol % to 43 mol %.

In addition to the foregoing components, a hydrophilic polymer or the like for improving retention in blood, fatty acid, diacetyl phosphate, or the like as a membrane structure stabilizer, or α-tocopherol or the like as an antioxidant may be added to the liposome. In the present invention, it is preferable not to include an additive such as a dispersion aid which is not recognized for use in intravenous injection in pharmaceutical applications, for example, a surfactant.

(Drug)

The liposome composition according to the embodiment of the present invention includes a drug.

The type of drug is not particularly limited, but anticancer agents given below can be used. Specific examples of the drug include anthracycline-based anticancer agents such as doxorubicin, daunorubicin, and epirubicin;

cisplatin-based anticancer agents such as cisplatin and oxaliplatin;

taxane-based anticancer agents such as paclitaxel and docetaxel;

vinca alkaloid-based anticancer agents such as vincristine and vinblastine;

bleomycin-based anticancer agents such as bleomycin;

sirolimus-based anticancer agents such as sirolimus;

caraptothecin-based anticancer agents such as topotecan (also referred to as nogitecan), irinotecan, karenitecin (registered trademark) (also referred to as BNP1350), exatecan, lurtotecan, gimatecan (also referred to as ST1481), and belotecan (also referred to as CKD602);

vinca alkaloid-based anticancer agents such as vincristine; and molecularly targeted drugs such as imatinib (Gleevec (registered trademark)), everolimus (Afinitor (registered trademark)), erlotinib (Tarceva (registered trademark)), gefitinib (Iressa (registered trademark)), sunitinib (Sutent (registered trademark)), sorafenib (Nexavar (registered trademark)), dasatinib (Sprycel (registered trademark)), tamibarotene (Amnolake (registered trademark)), tretinoin (Vesanoid (registered trademark)), bortezomib (Velcade (registered trademark)), and lapatinib (Tykerb (registered trademark)).

Among the foregoing drugs, topotecan (also referred to as nogitecan), doxorubicin, irinotecan, or sunitinib is preferable, and topotecan is more preferable.

Nogitecan hydrochloride (generic name, chemical name (+)-(4S)-10[-(dimethylamino)methyl]-4-ethyl-4,9-dihydroxy-1H-pyrano[3',4':6,7]indolizino[1, 2-b]quinoline-3,14 (4H,12H)-dione monohydrochloride) can be preferably applied as the topotecan, and is commercially available, for example, under a trade name of HYCAMTIN (registered trademark).

The drug may be used in the form of a salt.

Examples of the salt of the drug include salts in a basic group such as an amino group, and an acidic group such as a hydroxyl group or a carboxyl group, which are commonly known in the related art.

Examples of the salt in a basic group include salts with mineral acids such as hydrochloric acid, hydrobromic acid, phosphoric acid, boric acid, nitric acid, and sulfuric acid; salts with organic carboxylic acids such as formic acid, acetic acid, lactic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of the salt in an acidic group include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzyl amine, N-benzyl-β-phenethylamine, 1-ephenamine, and N,N'-dibenzylethylenediamine, The content of the drug in the liposome composition is not particularly limited, but is preferably 0.025 to 20 mg/ml and more preferably 0.25 to 10 mg/ml with respect to the liposome composition.

The amount of liposome-encapsulated drug relative to the liposome membrane-forming lipid is in a molar ratio of preferably 0.1 to 1.5 and more preferably 0.2. to 0.3 from the viewpoint of the release rate of the drug from the liposome, the osmotic pressure inside the liposome, and the liposome shape by the precipitated drug.

In a case where the molar ratio of the amount of drug to the lipid is too low, the area of the liposome membrane with respect to the unit drug amount is increased, the release rate of the drug from the liposome is increased, and therefore the function of improving the retention in blood is impaired. On the other hand, in a case where the molar ratio of the amount of drug to lipid is too high, the osmotic pressure inside the liposome is increased with an increased amount of the drug dissolved, thus resulting in destruction of the liposome, or in a case where the drug is precipitated inside the liposome, the precipitated solid grows large, thus resulting in deformation of the liposome shape.

(Ammonium Sulfate in Inner Water Phase)

The inner water phase of the liposome in the present invention contains ammonium sulfate. In addition, in the liposome composition which is the first embodiment of the present invention, the molar ratio of sulfate ions in the inner water phase to the drug in the entire water phase is 0.36 or more and preferably 0.4 or more. The molar ratio of sulfate ions in the inner water phase to the drug in the entire water phase is more preferably 0.4 or more and 1.8 or less and still more preferably 0.6 or more and 1.8 or less. By setting the molar ratio of sulfate ions in the inner water phase to the drug in the entire water phase as described above, it is possible to suppress leakage of the drug from the liposome in blood.

In a case where the molar ratio of sulfate ions in the inner water phase to the drug in the entire water phase is too low, this leads to incomplete formation of a solid of the drug due to the sulfate, an increased concentration of the drug in dissolved state, which results in increased permeability of the liposome membrane in the liposome, and easy leakage of the drug from the liposome, so that the effect of improving retention in blood is impaired. In addition, in a case where the molar ratio of sulfate ions in the inner water phase to the drug in the entire water phase is too high, the osmotic pressure inside the liposome will be high, resulting in the destruction of the liposome structure, so the drug is likely to leak out of the liposome and therefore the effect of improving retention in blood is impaired.

In addition, in the present invention, the percentage of sulfate ions contained in the inner water phase of the liposome to sulfate ions in the entire liposome composition (ratio of sulfate ions in inner water phase) is preferably at least 80% and more preferably 90% or more, and simultaneously the percentage of the drug contained in the inner water phase of the liposome to the drug in the entire liposome composition (ratio of drug in inner water phase) is preferably at least 80% and more preferably 90% or more.

The drug concentration in the liposome can be measured, for example, by liquid chromatography/UV-vis absorbance detection. In addition, the sulfate ion concentration in the inner water phase of the liposome can be measured, for example, by ion chromatography.

(pH of Outer Water Phase)

The liposome composition according to the embodiment of the present invention can include a liposome encapsulating a drug, and an aqueous solvent (outer water phase) in which the liposome is dispersed. The outer water phase preferably has a neutral pH and specifically a pH of about 5.5 to 8.5.

In a case where drug leakage is extremely suppressed, drug leakage at the affected area, particularly at the tumor site, may also be suppressed, and therefore the expected drug efficacy may not be obtained.

The liposome composition according to the embodiment of the present invention has a surprising mechanism of suppressing drug leakage in blood, delivering a sufficient amount of drug to the tumor site, and rapidly releasing the drug in the tumor site.

The tumor site has a property that an ammonium concentration is higher than that in other organs such as blood (see, for example, Nanomedicine: Nanotechnology, Biology, and Medicine, 11(2015) 1841-1850), and therefore the liposome composition according to the embodiment of the present invention may exhibit significantly increased drug release in an environment in which glutamine metabolism is enhanced and therefore an ammonium concentration is high (5 mmol/L), such as tumor.

The liposome composition according to the embodiment of the present invention has a drug release rate of 20%/24 hours or less at 37° C. from liposomes in plasma having an ammonium concentration of 1 mmol/L or less and a drug release rate of 60% or more at 37° C. from liposomes in plasma having an ammonium concentration of 4 to 6 mmol/L; and more preferably a drug release rate of 15%/24 hours or less at 37° C. from liposomes in plasma having an ammonium concentration of 1 mmol/L or less and a drug release rate of 70% or more at 37° C. from liposomes in plasma having an ammonium concentration of 4 to 6 mmol/L.

(Method for Producing Liposome Composition)

The method for producing the liposome composition according to the embodiment of the present invention is not particularly limited.

For example, the liposome composition according to the embodiment of the present invention can be produced by the following steps:

(a) preparation of an oil phase;
(b) preparation of a water phase;
(c) formation of liposome particles by emulsification;
(d) particle size regulation by extruder;
(e) replacement of liposome outer water phase liquid by dialysis;
(f) encapsulation of drug in liposome particles by remote loading; and
(g) removal of outer water phase drug by dialysis.

The particle size regulation by extruder (d) may or may not be carried out.

<(a) Preparation of Oil Phase>

(a) In the preparation of an oil phase, individual components (hydrophilic polymer-modified diacylphosphatidylethanolamine, dihydrosphingomyelin, and cholesterols) constituting the liposome and an organic solvent are mixed, and the mixture is heated to dissolve the components, whereby the oil phase can be produced.

Although the organic solvent used in the oil phase is not particularly limited, for example, a water-soluble organic solvent which is optionally mixed with water can be used.

Examples of the water-soluble organic solvent include alcohols such as methanol, ethanol, -propanol, isopropanol, n-butanol, isobutanol, and t-butanol; glycols such as glycerin, ethylene glycol, and propylene glycol, and polyalkylene glycols such as polyethylene glycol. Among these, alcohols are preferred. The alcohol is preferably at least one selected from ethanol, methanol, 2-propanol, or t-butanol, more preferably at least one selected from ethanol, 2-propanol, or t-butanol, and still more preferably ethanol.

The concentration of each component constituting the liposome is not particularly limited and can be appropriately adjusted.

<(b) Preparation of Water Phase>

Water (distilled water, water for injection, or the like), physiological saline, various buffer solutions or aqueous solutions of sugars (sucrose or the like), or mixtures thereof (aqueous solvent) can be used as the water phase. In the present invention, it is preferable to use an aqueous ammonium sulfate solution as the water phase, in a case where a drug is encapsulated in liposome particles by remote loading which will be described later.

The buffer solution is not limited to organic and inorganic buffer solutions, and a buffer solution having a buffering action in the vicinity of a hydrogen ion concentration close to that of the body fluid is suitably used and examples thereof include a phosphate buffer solution, a Tris buffer solution, a citrate buffer solution, an acetate buffer solution, and a Good's buffer solution. The inner water phase of the liposome may be an aqueous solution in which the liposomes are dispersed in a case of producing liposomes, or may be water, physiological saline, various buffer solutions, aqueous sugar solutions, or mixtures thereof which are newly added. The water used as an outer water phase or an inner water phase is preferably free from impurities (dust, chemicals, or the like).

The physiological saline refers to an inorganic salt solution adjusted to be isotonic with the human body fluid, and may further have a buffering function. Examples of the physiological saline include saline containing 0.9 w/v % (mass/volume percent) of sodium chloride, PBS, and Tris-buffered saline.

In the present invention, the water phase includes both an outer water phase and an inner water phase.

The outer water phase in the present invention means an aqueous solution in which liposomes are dispersed. For example, in a case of an injection, a solution occupying the outside of the liposome of a dispersion liquid of liposomes packaged and stored in a vial or prefilled syringe becomes an outer water phase. In addition, similarly for a liquid to be dispersed at the time of use in a case of being administered by means of an attached liquid for dispersion or other dissolution liquid, a solution occupying the outside of the liposome of a dispersion liquid of liposomes becomes an outer water phase.

The inner water phase in the present invention refers to a water phase in the closed vesicle across the lipid bilayer membrane of the liposome.

<(c) Formation of Liposome Particles by Emulsification>

In the emulsifying step, an oil phase and a water phase are mixed to prepare an aqueous solution containing lipids, which can be then emulsified with stirring. An oil phase where lipid has been dissolved in an organic solvent and a water phase are mixed, stirred, and emulsified to thereby prepare an emulsion where the oil phase and the water phase are emulsified in an O/W type (oil-in-water type). After mixing, liposomes are formed by removing a portion or all of the organic solvent derived from the oil phase by evaporation. Alternatively, a portion or all of the organic solvent in the oil phase is evaporated in the course of the stirring-emulsification to form liposomes.

As a method of stirring, ultrasonic waves or mechanical shearing force is used for particle miniaturization. In addition, extruder processing or microfluidizer processing of allowing to pass through a filter having a certain pore size can be carried out for uniformity of particle sizes. Use of an extruder or the like can result in decomposition of secondarily formed multivesicular liposomes into univesicular liposomes.

The emulsifying step is not limited as long as it is a step of emulsification, but it is preferably a step of applying a high shearing force and performing microparticulation with an emulsifying step including an organic solvent. The high shear rate is defined in terms of circumferential speed of a stirring blade of an emulsification machine and is preferably 5 m/s to 32 m/s and particularly preferably 20 m/s to 30 m/s. If necessary, evaporation (desolvation) of the organic solvent used in the emulsifying step may be carried out to form liposomes.

The liquid temperature in the emulsifying step in a case of producing liposomes can be appropriately adjusted, but the liquid temperature at the time of mixing an oil phase and a water phase is preferably equal to or higher than a phase transition temperature of the lipid to be used. For example, in a case where a lipid having a phase transition temperature of 35° C. to 40° C. is used, the liquid temperature at the time of mixing an oil phase and a water phase is preferably 35° C. to 70° C.

In the emulsifying step, the organic solvent and water may be evaporated from the aqueous solution containing the liposomes. As to the evaporation referred to herein, a portion or all of the organic solvent derived from the oil phase and the water derived from the water phase may be evaporated and forcibly removed, or a portion or all of the organic solvent derived from the oil phase and the water derived from the water phase may evaporate naturally during the course of stirring-emulsification.

The method of evaporation is not particularly limited, and for example, at least one of a step of heating to evaporate an organic solvent and water, a step of continuing the standing or slow stirring after emulsification, or a step of carrying out vacuum degassing may be carried out.

<(d) Particle Size Regulation by Extruder>

The obtained liposomes can be made uniform in particle size by using dialysis, filtration, extrusion processing, or the like.

The extrusion processing means a step of passing liposomes through a filter having a fine pore to apply a physical shearing force, thereby carrying out microparticulation of the liposomes. In a case where the Liposomes are passed through, rapid microparticulation thereof may be achieved by incubating the liposome dispersion liquid and the filter at a temperature higher than or equal to the phase transition temperature of the membrane constituting the liposome.

In addition, the particle size regulation by an extruder may or may not be carried out.

<(e) Replacement of Liposome Outer Water Phase Liquid by Dialysis>

In the present invention, in a case where the drug is encapsulated in the liposome particles by remote loading, the liposome outer water phase liquid may be replaced by dialysis. An aqueous solution of 0.05% to 5% by mass of NaCl can be used as a dialysis liquid which is not particularly limited. Dialysis of the liposome liquid using the above-mentioned dialysis liquid can provide liposomes in which ammonium sulfate present in the outer water phase is removed and the outer water phase is replaced with the dialysis liquid.

<(f) Encapsulation of Drug in Liposome Particles by Remote Loading Method>

In the present invention, it is preferable to encapsulate a drug in liposome particles by a remote loading method.

In the present invention, the remote loading method refers to a method of producing an empty liposome in which a drug is not encapsulated and then adding the drug to the liposome outer liquid to introduce the drug into the liposome. The method of remote loading is not particularly limited, but a method using an ammonium salt is preferable and a method using ammonium sulfate is more preferable.

In the remote loading method, the drug added to the outer liquid is actively transferred to liposomes and incorporated into the liposomes. A solubility gradient, an ion gradient, a pH gradient, or the like is used as the driving force. For example, there is a method of introducing a drug into liposomes using an ion gradient formed across a liposome membrane. For example, there is a technique of adding a drug into liposomes that are preformed by the remote loading method using a $Na^+/K^+$ concentration gradient.

Among the ion gradients, a proton concentration gradient is commonly used. For example, there is an aspect in which the inner (inner water phase) pH of the liposome membrane has a pH gradient lower than the outer (outer water phase) pH. The pH gradient can be specifically formed by a concentration gradient of ammonium ion gradient or the like.

<(g) Removal of Outer Water Phase Drug by Dialysis>

The drug-encapsulated liposome liquid may be subjected to dialysis to remove the drug not contained in the liposomes. For example, by subjecting the drug-encapsulated liposome liquid to dialysis, using a predetermined concentration of sucrose/histidine buffer as a dialysis liquid, the drug present in the outer water phase can be removed to obtain a liposome composition in which the outer water phase is replaced with the dialysis liquid.

<Sterile Filtration>

The liposome composition obtained above is preferably subjected to sterile filtration. Regarding the filtration method, it is possible to remove unwanted materials from an aqueous solution containing liposomes by using a hollow fiber membrane, a reverse osmosis membrane, a membrane filter, or the like. In the present invention, it is preferable to filter the liposome composition through a filter having sterilizable pore size (preferably a 0.2 μm filtration sterilization filter).

To prevent an effect of deformation of liposomes on the average particle size, the sterile filtration step and the below-described aseptic filling step are preferably carried out at a temperature lower than or equal to the phase transition temperature of the lipid constituting the liposome. For example, in a case where the phase transition temperature of the lipid is around 50° C., the sterile filtration step and the below-described aseptic filling step are carried out at temperature of preferably about 0° C. to 40° C., and more specifically about 5° C. to 30° C.

<Aseptic Filling>

The liposome composition obtained after sterile filtration is preferably aseptically filled for medical applications. Known methods can be applied for aseptic filling. A liposome composition suitable for medical applications can be prepared by aseptically filling the liposome composition in a container.

(Liposome Composition)

In connection with the route of administration, the Liposome composition according to the embodiment of the present invention may also contain at least one of a tonicity agent, a stabilizer, an antioxidant, or a pH adjusting agent which is pharmaceutically acceptable.

The tonicity agent is not particularly limited and examples thereof include inorganic salts such as sodium chloride, potassium chloride, sodium hydrogen phosphate, sodium dihydrogen phosphate, and potassium dihydrogen phosphate; polyols such as glycerol, mannitol, and sorbitol; and sugars such as glucose, fructose, lactose, and sucrose, The stabilizer is not particularly limited and examples thereof include sugars such as glycerol, mannitol, sorbitol, lactose, and sucrose.

The antioxidant is not particularly limited and examples thereof include ascorbic acid, uric acid, tocopherol homologues (for example, vitamin E, four tocopherol isomers α, β, γ, and δ), cysteine, and ethylenediaminetetraacetic acid (EDTA). Stabilizers and antioxidants may be respectively used alone or in combination of two or more thereof.

Examples of the pH adjusting agent include sodium hydroxide, citric acid, acetic acid, triethanolamine, sodium hydrogen phosphate, sodium dihydrogen phosphate, and potassium dihydrogen phosphate.

The liposome composition according to the embodiment of the present invention may contain an organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerin, propylene glycol, polyethylene glycol, vaseline, paraffin, stearyl alcohol, stearic acid, human serum albumin (HSA), mannitol, sorbitol, lactose, phosphate-buffered saline (PBS), sodium chloride, sugars, a biodegradable polymer, a serum-free medium, each of which is pharmaceutically acceptable, or an additive which is acceptable as a pharmaceutical additive.

The container in which the liposome composition according to the embodiment of the present invention is filled is not particularly limited, and it is preferably made out of a material having low oxygen permeability. Examples of the container include a plastic container, a glass container, and a laminated film bag with an aluminum foil, an aluminum vapor deposition film, an aluminum oxide vapor deposition film, a silicon oxide vapor deposition film, a polyvinyl alcohol, an ethylene-vinyl alcohol copolymer, a polyethylene terephthalate, a polyethylene naphthalate, a polyvinylidene chloride, or the like as a gas barrier layer. The container can be shielded from light by employing, for example, a bag using a colored glass, an aluminum foil, an aluminum vapor deposition film, or the like, if necessary.

In the container in which the liposome composition is filled, in order to prevent oxidation due to oxygen existing in the space inside the container, it is preferable to replace the gas in the container space and drug solution with an inert gas such as nitrogen. For example, an injection solution is bubbled with nitrogen, whereby the filling of the injection solution into a container can be carried out under a nitrogen atmosphere.

The administration route of the liposome composition according to the embodiment of the present invention is preferably parenteral administration. Examples of the parenteral administration include intravenous injection such as intravenous drip, intramuscular injection, intraperitoneal injection, subcutaneous injection, intraocular injection, and intrathecal injection. The administration method of the liposome composition may be, for example, administration by syringe or intravenous drip.

The dosage and frequency of administration of the liposome composition according to the embodiment of the present invention may be appropriately set depending on the type of drug, the condition of the patient, and the like. The dose of the liposome composition can be generally set in the range of 0.01 mg/kg/day to 100 mg/kg/day in terms of the mass of drug which is an active ingredient. The dose of the liposome composition can be set in the range of 2 mg to 10 mg per dose in terms of the mass of drug which is an active ingredient, but it is not limited to these dosages.

((B) Immune Checkpoint Inhibitor)

The term "immune checkpoint inhibitor" refers to a drug that acts on an immune checkpoint molecule or a ligand thereof to inhibit signal transduction by the immune checkpoint molecule. Examples of target molecules of the immune checkpoint inhibitor include immune checkpoint molecules and ligands thereof that are presented on the surface of T cells and antigen-presenting cells, specifically, molecules such as PD-1, CTLA-4, TIM3, LAG3, PD-L1, PD-L2, BTNL2, B7-H3, B7-H4, CD48, CD80, 2B4, BTLA, CD160, CD60, CD86, and VISTA, but the present invention is not limited thereto. In the present invention, the immune checkpoint inhibitor is preferably an agent that inhibits at least one selected from programmed cell death protein 1 (PD-1) or a ligand thereof PD-L1 or PD-L2, or cytotoxic T lymphocyte antigen 4 (CTLA-4). PD-1 (Programmed death-1, CD279) is a 50-55 kDa type I membrane protein belonging to the CD28/CTLA-4 family that acts to enhance/suppress lymphocyte activation signals. In addition, PD-L1 (also known as B7-H1 or CD274) and PD-L2 (also known as B7-DC or CD273) are ligands of PD-1 expressed on the surface of antigen-presenting cells.

The immune checkpoint inhibitor may be any substance capable of inhibiting the function of an immune checkpoint molecule and a ligand thereof presented on the surface of T cells or antigen-presenting cells. For example, at least one of an anti-PD-1 antibody, an anti-PD-L1 antibody, an anti-PD-L2 antibody, or an anti-CTLA-4 antibody known in the related art can be used. An anti-PD-1 antibody, an anti-PD-L1 antibody, an anti-PD-L2 antibody, an anti-CTLA-4 antibody, and the like are commercially available from, for example, Bio X Cell. Specific examples of the immune checkpoint inhibitor include, but are not limited to, nivolumab, pembrolizumab, ipilimumab, atezolizumab, durvalumab, avelumab, and tremelimumab. In addition, it is also possible to use at least one of an anti-PD-1 antibody, an anti-PD-L1 antibody, or an anti-PD-L2 antibody in combination with an anti-CTLA-4 antibody, as the immune checkpoint inhibitor.

The immune checkpoint inhibitor according to the embodiment of the present invention can be administered to a subject by oral or parenteral administration and preferably parenteral administration. The administration method specifically includes injection administration, nasal administration, pulmonary administration, transdermal administration, and the like. Examples of the injection administration include intravenous injection, intramuscular injection, intraperitoneal injection, and subcutaneous injection. In addition, the administration method can be appropriately selected depending on the age and symptoms of the subject. The dose can be selected, for example, in the range of 0.0001 mg to 1,000 mg per kg subject body weight per administration. Alternatively, the dose can be selected within the range of 0.001 mg/body to 100,000 mg/body per patient. In a case where the immune checkpoint inhibitor according to the embodiment of the present invention is administered simultaneously or sequentially in combination with the liposome composition according to the embodiment of the present invention, the effective dose and dosing period of the immune checkpoint inhibitor can be selected so as to exhibit a therapeutic synergistic effect. However, the present invention is not limited to these doses.

(Additives and the Like for Immune Checkpoint Inhibitor)

The immune checkpoint inhibitor according to the embodiment of the present invention can be prepared by adding additives including a medium such as a pharmaceutically acceptable aqueous solution, a salt, a preservative, a buffer, and the like for administration thereof to a subject, in addition to an anti-PD-1 antibody, an anti-PD-L1 antibody, an anti-PD-L2 antibody, an anti-CTLA-4 antibody, and the like. Specifically, the above-mentioned additives and the like of the liposome composition according to the embodiment of the present invention can be similarly applied.

The pharmaceutical formulation according to the embodiment of the present invention can be used to treat a subject having a cancer that is refractory to treatment with an immune checkpoint inhibitor. For example, a subject for whom a desired drug efficacy was not observed by the administration of the immune checkpoint inhibitor can be treated with the pharmaceutical formulation according to the embodiment of the present invention.

Although the mechanism of action of the pharmaceutical formulation according to the embodiment of the present invention is unknown, it is presumed to be as follows, but is not limited thereto. It is presumed that the pharmaceutical formulation according to the embodiment of the present invention has an excellent growth inhibitory effect on tumor cells, due to art EPR effect in which drug-encapsulated liposomes permeate through the interstitial spaces of endothelial cells that make up neovascular vessels existing around tumors and are accumulated and retained in tumor tissues.

In addition, it is presumed that the immune checkpoint inhibitor enhances the immunity against cancer by inhibiting the function of an immune checkpoint molecule such as CTLA-4 or PD-1 or a ligand thereof PD-L1 or PD-L2, whereby the progression of cancer can be suppressed or the cancer can be treated.

Furthermore, by simultaneously or sequentially administering a drug-containing liposome composition and an immune checkpoint inhibitor in combination, the pharmaceutical formulation according to the embodiment of the present invention has a stronger antitumor effect (for example, tumor growth inhibitory effect) by using single agents (a drug-containing liposome composition and an immune checkpoint inhibitor) in combination as compared with each of the single agents.

The pharmaceutical formulation according to the embodiment of the present invention can be used as a pharmaceutical formulation in which a drug-containing liposome composition and an immune checkpoint inhibitor are combined and administered simultaneously or sequentially, and preferably as an anticancer agent.

The type of cancer to which the pharmaceutical formulation according to the embodiment of the present invention is applied is not particularly limited, and examples thereof include lung cancer (especially small cell lung cancer), ovarian cancer, pediatric solid tumor, uterine cervical cancer, breast cancer, prostate cancer, endometrial cancer, gastric cancer (gastric adenocarcinoma), non-small cell lung cancer, pancreatic cancer, cervical squamous cell carcinoma, esophageal cancer, bladder cancer, melanoma, colon cancer, renal cell cancer, non-Hodgkin's lymphoma, urothelial cancer, multiple myeloma, acute myeloid leukemia, chronic myeloid leukemia, acute lymphocytic leukemia, adult T cell leukemia, bone marrow metastatic cancer, sarcoma, soft tissue tumor, chronic myelomonocytic leukemia, Hodgkin's lymphoma, and cutaneous T cell lymph.

The resistance means that cancer cells show resistance to an anticancer agent and includes the natural resistance to which the anticancer agent does not work from the beginning of treatment and a condition in which an initially effective anticancer agent is ineffective or diminishes in effect as the treatment continues. Specifically, the resistance refers to a property that cells did not show an appropriate response to an anticancer agent in that the cells responded to the anticancer agent in the early stage, but then showed a decrease in responsiveness during the treatment, or in that the cells continued to proliferate during the treatment with the anticancer agent.

The pharmaceutical formulation according to the embodiment of the present invention can exert an excellent effect on topotecan-resistant cancer. The breast cancer resistance protein (BCRP) is a member of the ATP-binding cassette (ABC) transporter protein family. This transporter protein directs an efflux of an anticancer agent from cancer cells and reduces an intracellular concentration of the anticancer agent, thus reducing or eliminating a desired anticancer effect of the drug in these resistant cancer cells. It is speculated that the pharmaceutical formulation according to the embodiment of the present invention can exert an excellent effect on topotecan-resistant cancer by achieving exposure of tumor cells to a high concentration of topotecan over a long period of time due to the EPR effect that the drug is accumulated and retained in tumor tissues.

(Tumor Volume)

In the present invention, a tumor can be transplanted into a model animal (preferably a mouse or a rat) in order to measure the tumor volume. Inhibition of tumor volume growth depends on the drug used, the combination of lipids or the like constituting the liposome, and the effective amount. The inhibition of tumor volume growth refers to at least one of inhibiting tumor growth, achieving tumor stasis, or achieving substantial or complete tumor regression.

In a case where the liposome composition according to the embodiment of the present invention is administered to a subject such as a mammal, the administration can be started after assignment of model animals into a treatment group and a control group, and then transplantation of tumor cells into the subject animals, for example, growth of the tumor cells to 100 to 1,000 mm such that the tumor cells settle.

For example, in a case where the model animal is a mouse, mice in each group can be weighed as a whole daily until the animals reach a minimum body weight, as an evaluation of the liposome composition according to the embodiment of the present invention.

Tumors can be measured with calipers or the like until final sacrifice of the animals for sampling, until tumors reach 2,000 mm$^3$, or until the animals die. The tumor volume in a mammalian subject can be measured using any method recognized in the related art.

For example, caliper measurement can be used to evaluate the tumor volume using the expression: $(a \times b^2) \times 0.5$, where "a" is a maximum diameter and "b" is a minor axis length. In addition, in a case of humans, the tumor volume can be measured by a technique for diagnostic imaging such as computer tomography (CT) scanning or magnetic resonance imaging (MRI) scanning.

EXAMPLES

Hereinafter, the present invention will be specifically described with reference to Examples, but the present invention is not limited thereto. It is understood that the present invention can be variously changed and modified by those skilled in the art. Unless such changes and modifications depart from the scope of the present invention, those changes and modifications are included in the present invention. Various reagents used in the Examples are commercially available unless otherwise specified.

SM represents sphingomyelin (COATSOME NM-10, manufactured by NOF Corporation).

Chicken egg-derived. DHSM represents dihydrosphingomyelin obtained by hydrogenating chicken egg-derived SM (synthetic product obtained by hydrogenating COATSOME NM-10 (manufactured by NOF Corporation)). This chicken egg-derived DHSM is a mixture containing DHSM having two alkyl chains having 16 carbon atoms, which accounts for 70% to 80% of a total of the chicken egg-derived DHSM, and DHSM having different alkyl chain lengths, which is the remainder.

Totally synthetic DHSM represents dihydrosphingomyelin produced by chemical synthesis so as to contain 98% or more of the following compound having a long-chain alkyl group having 16 carbon atoms and a long-chain alkyl group having 18 carbon atoms.

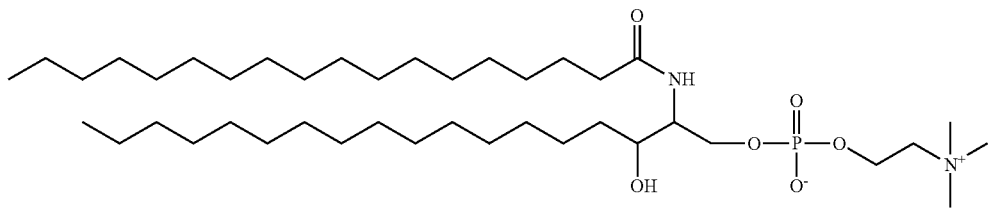 [SMILES: CCCCCCCCCCCCCCCCCC(=O)NC(COP(=O)([O-])OCC[N+](C)(C)C)C(O)CCCCCCCCCCCCCCC]

SUNBRIGHT DSPE-020CN (hereinafter referred to as DSPE-PEG, manufactured by NOF Corporation) was used as PEG phospholipid (denoted as PEG in the table).

Cholesterol HP (manufactured by Nippon Fine Chemical Co., Ltd.) was used as cholesterol (denoted as Chol in the table).

Comparative Examples 1 to 10

(a) Preparation of Oil Phase

For Comparative Example 1, 11.52 g of SM, 4.32 g of PEG phospholipid, and 4.32 g of cholesterol were respectively weighed. For Comparative Examples 2 to 10, the amounts of SM or chicken egg-derived DHSM, PEG phospholipid, and cholesterol were changed to the ratios described in Table 1. The lipid was mixed with 381 mL of ethanol and dissolved at 65° C. to prepare an oil phase.

(b1) Preparation of Water Phase 1

25.2 g of ammonium sulfate was dissolved in 1118.5 g of water to prepare water phase 1.

(b2) Preparation of Water Phase 2

5.04 g of ammonium sulfate was dissolved in 223.7 g of water to prepare water phase 2.

(c) Formation of Liposome Particles by Emulsification

The water phase 1 prepared in (b1) was heated to 65° C., the whole of the oil phase prepared in (a) was added thereto, and then these phases were mixed with a precision emulsification disperser at a circumferential speed of 26 m/s for 60 minutes. Subsequently, the water phase 2 at room temperature was added thereto, followed by continuing the stirring at a circumferential speed of 0.1 m/s while heating at 65° C. to evaporate the organic solvent and water. In a case where the liquid was concentrated to 600 mL, the heating and stirring were stopped and therefore the evaporation was terminated.

(e) Replacement of Liposome Outer Water Phase Liquid by Dialysis

An aqueous solution of 3.15% by mass NaCl was used as a dialysis liquid. Using this dialysis liquid, the liquid obtained in (c) was subjected to cross-flow filtration at room temperature to remove ammonium sulfate present in the outer water phase to obtain liposomes in which the outer water phase was replaced with the dialysis liquid.

(f) Encapsulation of Topotecan Liposome Particles by Remote Loading

Water for injection was added to topotecan hydrochloride (manufactured by Biocompounds Pharmaceutical Inc.) to 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 60 minutes.

(g) Removal of Outer Water Phase Topotecan by Dialysis

A sucrose: histidine; buffer consisting of 9.4% by mass sucrose and 10 mmol/L histidine was prepared as a dialysis liquid. Using this dialysis liquid, the liquid obtained in (f) was subjected to cross-flow filtration at room temperature to remove topotecan present in the outer water phase to obtain topotecan-containing liposomes in which the outer water phase was replaced with the dialysis liquid.

Comparative Examples 11 and 12

(a) Preparation of Oil Phase

For Comparative Example 11, 0.517 g of chicken egg-derived DHSM and 0.233 g of cholesterol were respectively weighed. For Comparative Example 12, the amounts of SM and cholesterol were changed to the ratios described in Table 1. In order to label liposomes with DiI (1,1'-dioctadecyl-3,3,3',3'-tetramethylindocarbocyanine perchlorate), an amount of DiI, which was 0.2 mol % with respect to total lipids, was weighed and dissolved in ethanol. Ethanol was added to the DiI ethanol solution to make a total volume of 1.5 mL, and the weighed lipid and this organic solvent were mixed and heated to 65° C. to dissolve the lipid and form an oil phase.

(b) Preparation of Water Phase 0.9 g of ammonium sulfate and 2.16 g of sucrose were dissolved in 13.5 g of water to prepare a water phase.

(c) Formation of Liposome Particles by Mixing Oil Phase and Water Phase

The water phase prepared in (b) was heated to 65° C. and stirred with a magnetic stirrer (3,000 rpm). The whole oil phase prepared in (a) was heated to 65° C. with a hot plate, and the whole oil phase was sucked with a syringe and heated for 5 minutes with a hot plate. The oil phase was added dropwise over 30 seconds to the heated water phase.

(d) Particle Size Regulation by Extruder

The liquid obtained in (c) was subjected to the particle size regulation by sequentially passing it through a filter using an extruder (Mini Extruder, manufactured by Avanti Polar Lipids, Inc.) under heating at 70° C.

(e) Replacement of Liposome Outer Water Phase Liquid by Dialysis

An aqueous solution of 0.09% by mass of NaCl was used as a dialysis liquid. Using this dialysis liquid, the liquid obtained in (c) or (d) was subjected to dialysis at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 120 minutes.

(g) Removal of Outer Water Phase Topotecan by Dialysis

A sucrose/histidine buffer consisting of 9.4% by mass sucrose and 10 mol/L histidine was prepared as a dialysis liquid. Using this dialysis liquid, the liquid obtained in (f) was subjected to dialysis at room temperature to remove topotecan present in the outer water phase to obtain topotecan-containing liposomes in which the outer water phase was replaced with the dialysis liquid.

Examples 1 to 8

(a) Preparation of Oil Phase

For Example 1, 11.52 g of chicken egg-derived DHSM, 4.32 g of PEG phospholipid (SUNBRIGHT DSPE-020CN, manufactured by NOF Corporation, hereinafter referred to as DSPE-PEG), and 4.32 g of cholesterol were respectively weighed. For Examples 2 to 8, the amounts of DHSM, DSPE-PEG, and cholesterol were changed to the ratios described in Table 2. The lipid was mixed with 381 mL of ethanol and dissolved at 65° C. to prepare an oil phase.

(b1) Preparation of Water Phase 1

25.2 g of ammonium sulfate was dissolved in 1118.5 g of water to prepare water phase 1.

(b2) Preparation of Water Phase 2

5.04 g of ammonium sulfate was dissolved in 223.7 g of water to prepare water phase 2.

(c) Formation of Liposome Particles by Emulsification

The water phase 1 prepared in (b1) was heated to 65° C., the whole of the oil phase prepared in (a) was added thereto, and then these phases were mixed with a precision emulsification disperser at a circumferential speed of 26 m/s for 60 minutes. Subsequently, the water phase 2 at room temperature was added thereto, followed by continuing the stirring at a circumferential speed of 0.1 m/s while heating at 65° C. to evaporate the organic solvent and water. In a case where the liquid was concentrated to 600 mL, the heating and stirring were stopped and therefore the evaporation was terminated.

(e) Replacement of Liposome Outer Water Phase Liquid by Dialysis

An aqueous solution of 3.15% by mass NaCl was used as a dialysis liquid. Using this dialysis liquid, the liquid obtained in (c) was subjected to cross-flow filtration at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 60 minutes.

(g) Removal of Outer Water Phase Topotecan by Dialysis

A sucrose/histidine buffer consisting of 9.4% by mass sucrose and 10 mmol/L histidine was prepared as a dialysis liquid. Using this dialysis liquid, the liquid obtained in (f) was subjected to cross-flow filtration at room temperature to remove topotecan present in the outer water phase to obtain topotecan-containing liposomes in which the outer water phase was replaced with the dialysis liquid.

Examples 9 and 10

(a) Preparation of Oil Phase

For Example 9, 0.412 g of chicken egg-derived DHSM, 0.153 a of DSPE-PEG, and 0.153 g of cholesterol were respectively weighed. For Example 10, the amounts of chicken egg-derived DHSM, DSPE-PEG, and cholesterol were changed to the ratios described in Table 2. In order to label liposomes with DiI, an amount of DiI, which was 0.2 mol % with respect to total lipids, was weighed and dissolved in ethanol. Ethanol was added to the resulting DiI ethanol solution to make a total volume of 11.25 mL, and 3.75 mL of ethyl acetate was further added thereto. The weighed lipid and this organic solvent were mixed and heated to 60° C. to dissolve the lipid, thus preparing an oil phase.

(b) Preparation of Water Phase 0.9 g of ammonium sulfate was dissolved in 40 g of water to prepare a water phase.

(c) Formation of Liposome Particles by Emulsification

The water phase prepared in (b) was heated to 70° C., the whole of the oil phase prepared in (a) was added thereto (volume ratio: water phase/oil phase=8/3), and then these phases were mixed using an emulsification machine (Excel Auto homogenizer ED-3, manufactured by Nippon Seiki Seisakusho Ltd.) at 3,000 rpm (rotation per minute: $\frac{1}{60}s^{-1}$) for 30 minutes. This was followed by continuing the stirring at 300 rpm while heating at 65° C. to evaporate the organic solvent and water. In a case where the liquid was concentrated to 15 g, the heating and stirring were stopped and therefore the evaporation was terminated.

(d) Particle Size Regulation by Extruder

The liquid obtained in (c) was subjected to the particle size regulation by sequentially passing it through a filter using an extruder (Mini Extruder, manufactured by Avanti Polar Lipids, Inc.) under heating at 70° C.

(e) Replacement of Liposome Outer Water Phase Liquid by Dialysis

An aqueous solution of 0.09% by mass of NaCl was used as a dialysis liquid. Using this dialysis liquid, the liquid obtained in (c) or (d) was subjected to dialysis at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 120 minutes.

(g) Removal of Outer Water Phase Topotecan by Dialysis

A sucrose/histidine buffer consisting of 9.4% by mass sucrose and 10 mmol/L histidine was prepared as a dialysis liquid. Using this dialysis liquid, the liquid obtained in (f) was subjected to dialysis at room temperature to remove topotecan present in the outer water phase to obtain topotecan-containing liposomes in which the outer water phase was replaced with the dialysis liquid.

[Measurement and Evaluation of Physical Properties]

<Average Particle Size>

In the present invention, the average particle size refers to a cumulant average particle size measured by a dynamic light scattering method. The average particle size in each of Examples and Comparative Examples described in table is a cumulant average particle size measured by a dynamic light scattering method using a concentrated system particle size analyzer FPAR-1000AS (manufactured by Otsuka Electronics Co., Ltd.) with an autosampler. The measurement results are shown in Tables 1 and 2.

<Topotecan Concentration Measurement>

Tables 1 and 2 show the results of quantifying the concentration of topotecan by measuring a sample with a high performance liquid chromatography (HPLC) apparatus Nexera-i LC-2040C (manufactured by Shimadzu Corporation). The specific measurement method is as follows.

In the liposomes of Tables 1 and 2, the percentage of the drug contained in the inner water phase of the liposome to the drug in the entire liposome composition was at least 95%, except for Comparative Example 10. For Comparative Example 10, the percentage of the drug contained in the inner water phase of the liposome to the drug in the entire liposome composition was 59%.

Measurement of Amount of Topotecan in Liposome Preparation

The prepared liposome liquid was dissolved in methanol and then filtered to prepare a sample solution, and topotecan hydrochloride was diluted to prepare a calibration curve standard solution. Using the sample solution and the calibration curve standard solution thus prepared, the amount of topotecan in liposome preparation was measured by liquid chromatography/UV-vis absorbance detection.

The concentration of topotecan in the inner water phase was calculated by subtracting the concentration of topotecan in the outer water phase from the concentration of topotecan in the entire water phase.

The concentration of topotecan in each water phase was measured as follows.

(Concentration of Topotecan in Entire Water Phase)

50 µL of the liposome dispersion liquid was measured and 950 of methanol was added thereto, followed by stirring with a vortex for 1 minute. 100 µL was measured from the liquid and 900 µL of Milli-Q water was added thereto, followed by stirring with a vortex for 1 minute to prepare a sample for HPLC analysis.

(Concentration of Topotecan in Outer Water Phase)

50 µL of the liposome dispersion liquid was measured and then diluted by adding 450 µl of a 9.4 wt % sucrose/10 mM histidine aqueous solution. 200 µL of PBS was added to 100 µL of the diluted liquid which was then mixed by inversion. The dispersion liquid was ultracentrifuged (200,000 g, 20° C., 60 minutes), and the supernatant was used as an HPLC analysis sample. The ultracentrifuge used was Himac CP80WX (manufactured by Hitachi, Ltd).

a) Preparation of Calibration Curve Standard Solution

About 2.0 mg of topotecan hydrochloride was weighed and dissolved in 20 mL of 10% by mass methanol aqueous solution. Milli-Q water was added to this liquid to prepare a solution having a topotecan hydrochloride concentration of 0.1, 1.0, 5.0, 10.0, 20.0, 50.0, or 100.0 ppm, which was then used as a calibration curve standard solution.

b) Preparation of Sample Solution (1) About 50 µL of a sample liposome preparation solution) was weighed by MICROMAN (registered trademark), and about 950 µL of methanol weighed by MIC ROMAN was added thereto. After it was shaken for about 1 minute, the solution was visually confirmed to become clear.

(2) 100 µL of the solution of the above (1) was weighed by MICROMAN, and about 900 µL of Milli-Q water weighed by a micropipette was added thereto. This liquid was shaken for about 1 minute, sonicated for about 1 minute, and further shaken for about 10 seconds.

(3) The solution obtained by filtering the solution of the above (2) through a DISMIC (registered trademark) filter (pore diameter: 0.45 μm) was used as a sample solution.

c) Measurement

The measurement was carried out under the following conditions chromatography/UV-vis absorbance detection.

Measurement wavelength: 382 nm, column: Shiseido CAPCELLPAK C18 ACR 3 μm_3.0 mm*75 mm Column temperature: constant temperature of around 40° C.

Both of mobile, phases A and B are a water/methanol/trifluoroacetic acid mixture, and feeding of the mobile phases was carried out by changing the mixing ratio of mobile phases A and B to control a concentration gradient.

Measurement was carried out under the conditions of a flow rate: 1.0 mL/minute, an injection volume: 10 μL, and an autosampler temperature: constant temperature of around 25° C.

<Measurement of Sulfate Ion Concentration>

The sample was measured with an ion chromatography apparatus 883 Basic IC plus (manufactured by Metrohm AG) to quantify the concentration of sulfate ions. The results of measuring the molar ratio of sulfate ions to topotecan are shown in Tables 1 and 2. In the liposomes of Tables 1 and 2, the percentage of sulfate ions contained in the inner water phase of the liposome to sulfate ions in the entire liposome composition was at least 90%.

The concentration of sulfate ions in the inner water phase was calculated by subtracting the concentration of sulfate ions in the outer water phase from the concentration of sulfate ions in the entire water phase. The concentration of sulfate ions in each water phase was measured as follows.

(Concentration of Sulfate Ions in Entire Water Phase)

50 μL of the liposome dispersion liquid was measured and 950 μL of methanol was added thereto, followed by mixing with ultrasonication for 15 seconds. 90 μL was measured from the liquid and 810 μL of water for injection (manufactured by Hikari Pharmaceutical Co., Ltd.) was added thereto, followed by mixing with ultrasonication for 30 seconds. 900 μL of ethyl acetate was added to the resulting solution which was then shaken well to extract lipids into an ethyl acetate phase. An appropriate amount of the water phase liquid was measured and used for ion chromatography analysis.

(Concentration of Sulfate Ions in Outer Water Phase)

100 μL of the liposome dispersion liquid was measured and then diluted by adding 900 μL of 5% glucose solution (manufactured by Otsuka Pharmaceutical Co., Ltd.). 450 μL of the resulting liquid was treated by ultrafiltration, and the filtrate was used as an ion chromatography analysis sample.

Centrifugation conditions were 7,400 g, 5° C., and 30 minutes. The centrifuge used was Himac CF15RXII (manufactured by Hitachi, Ltd).

<Measurement of AUC>

The mice to which the prepared topotecan-containing liposomes were administered (dose: 1 mg/kg in terms of the amount of drug) were bled at 0.25, 2, 6, and 24 hours after administration. The blood was centrifuged at 800×g for 10 minutes to recover plasma. The concentration of topotecan was quantified for the collected plasma using liquid chromatography/mass spectrometry/mass spectrometry (LC/MS/MS). Using the pharmacokinetic analysis software WinNonlin (registered trademark) (available from Certara, L.P.), the area under blood concentration-time curve (AUC) up to infinite time after single administration was calculated from the transition of the topotecan concentration thus obtained. The unit of AUC is time×ng/mL (expressed as hr*ng/mL in the table). In addition, the AUC of the liposome described in ["ONO ONCOLOGY Opdivo Q&A, Can Opdivo be used in combination with chemotherapeutic agents?", [online], publication date unknown, Ono Pharmaceutical Co., Ltd., [Search on May 2, 2018], Internet <URL: https://www.ono-oncology.jp/contents/patient/opdivo_faq/11.html>] is calculated to be 68152 hours×ng/mL.

TABLE 1

| | Average particle size | Concentration of topotecan in entire water phase | $SO_4^{2-}$ in inner water phase/ topotecan in entire water phase | Molar ratio of constitutional components of liposome membrane | | | | Dose | AUC | Percentage of topotecan in inner water phase | Percentage of $SO_4^{2-}$ in inner water phase |
|---|---|---|---|---|---|---|---|---|---|---|---|
| | nm | ppm | mol/mol | PEG | Chol | DHSM | SM | mg/kg | hr*ng/mL | % | % |
| Comparative Example 1 | 101.7 | 2419 | 0.70 | 4.7% | 37% | 0% | 58% | 1.0 | 120189 | 99 | 100 |
| Comparative Example 2 | 96.3 | 2605 | 0.75 | 4.8% | 42% | 0% | 53% | 1.0 | 136669 | 100 | 100 |
| Comparative Example 3 | 90.2 | 2993 | 1.57 | 4.5% | 42% | 0% | 54% | 1.0 | 140108 | 100 | 98 |
| Comparative Example 4 | 105.2 | 2889 | 1.58 | 4.6% | 47% | 0% | 48% | 1.0 | 137082 | 100 | 98 |
| Comparative Example 5 | 91.1 | 2946 | 1.01 | 4.9% | 47% | 0% | 48% | 1.0 | 157878 | 100 | 96 |
| Comparative Example 6 | 99.3 | 2994 | 1.01 | 4.7% | 39% | 0% | 56% | 1.0 | 143615 | 100 | 100 |
| Comparative Example 7 | 101.2 | 3080 | 0.96 | 4.7% | 39% | 0% | 56% | 1.0 | 119518 | 100 | 98 |
| Comparative Example 8 | 100.8 | 2437 | 1.14 | 4.7% | 39% | 0% | 57% | 1.0 | 173179 | 100 | 98 |
| Comparative Example 9 | 90.8 | 1191 | 0.32 | 5.0% | 38% | 57% | 0% | 1.0 | 140277 | 100 | 100 |
| Comparative Example 10 | 131.2 | 1328 | 0.3 | 4.4% | 36% | 59% | 0% | 1.0 | 174087 | 59 | 100 |

TABLE 1-continued

|  | Average particle size | Concentration of topotecan in entire water phase | SO$_4^{2-}$ in inner water phase/ topotecan in entire water phase | Molar ratio of constitutional components of liposome membrane | | | | Dose | AUC | Percentage of topotecan in inner water phase | Percentage of SO$_4^{2-}$ in inner water phase |
|---|---|---|---|---|---|---|---|---|---|---|---|
|  | nm | ppm | mol/mol | PEG | Chol | DHSM | SM | mg/kg | hr*ng/mL | % | % |
| Comparative Example 11 | 106 | 1876 | — | 0% | 43% | 57% | 0% | 1.0 | 182694 | 99 | — |
| Comparative Example 12 | 111.2 | 2437 | — | 0% | 45% | 0% | 55% | 1.0 | 134591 | 100 | — |

TABLE 2

|  | Average particle size | Concentration of topotecan in entire water phase | SO$_4^{2-}$ in inner water phase/ topotecan in entire water phase | Molar ratio of constitutional components of liposome membrane | | | | Dose | AUC | Percentage of topotecan in inner water phase | Percentage of SO$_4^{2-}$ in inner water phase |
|---|---|---|---|---|---|---|---|---|---|---|---|
|  | nm | ppm | mol/mol | PEG | Chol | DHSM | SM | mg/kg | hr*ng/mL | % | % |
| Example 1 | 100 | 2160 | 0.66 | 5.6% | 40% | 54% | 0% | 1.0 | 227895 | 99 | 97 |
| Example 2 | 122 | 2347 | 1.38 | 5.3% | 39% | 56% | 0% | 1.0 | 201264 | 100 | 100 |
| Example 3 | 88 | 2353 | 1.16 | 5.4% | 38% | 56% | 0% | 1.0 | 270579 | 99 | 100 |
| Example 4 | 111.3 | 2167 | 1.05 | 5.2% | 38% | 57% | 0% | 1.0 | 295476 | 99 | 98 |
| Example 5 | 115.9 | 2659 | 0.8 | 5.1% | 35% | 60% | 0% | 1.0 | 330913 | 100 | 100 |
| Example 6 | 125.2 | 1349 | 0.9 | 4.4% | 36% | 60% | 0% | 1.0 | 261345 | 99 | 100 |
| Example 7 | 120.3 | 3984 | 0.6 | 5.0% | 43% | 52% | 0% | 1.0 | 278684 | 98 | 98 |
| Example 8 | 116.8 | 2254 | 1.1 | 5.1% | 43% | 52% | 0% | 1.0 | 307412 | 99 | 98 |
| Example 9 | 101 | 1561 | 0.73 | 10.0% | 40% | 50% | 0% | 1.0 | 245450 | 100 | 100 |
| Example 10 | 104 | 1758 | 0.68 | 5.1% | 40% | 55% | 0% | 1.0 | 270294 | 100 | 92 |

As can be seen from the results in Tables 1 and 2, in Examples 1 to 10 of the liposome composition including a hydrophilic polymer-modified diacylphosphatidylethanolamine, a dihydrosphingomyelin, and cholesterol as constitutional components of a liposome membrane, in which an inner water phase contains ammonium sulfate, and a molar ratio of sulfate ions in the inner water phase to the drug in the entire water phase is 0.36 or more, it was shown that the measured value of AUC is 200,000 or more and therefore high retention in blood can be achieved.

On the other hand, in Comparative Examples 1 to 8 in which dihydrosphingomyelin is not used, Comparative Examples 9 and 10 in which the molar ratio of sulfate ions in the inner water phase to the drug in the entire water phase is less than 0.36, and Comparative Examples 11 and 12 in which hydrophilic polymer-modified diacylphosphatidylethanolamine is not used, it was shown that the measured value of AUC is less than 200,000, which is inferior to Examples 1 to 10.

(Composition of Topotecan-Containing Liposome Composition (Hereinafter, also Referred to as Liposome Composition According to Embodiment of Present Invention or Lipo))

Topotecan hydrochloride: 20 mg
HSPC (Note 1): 95.8 mg
MPEG-DSPE (Note 2): 31.9 mg
Cholesterol: 31.9 mg
Ammonium sulfate: 20 mg
L-histidine: 15.5 mg
Purified white sugar: 940 mg
pH adjusting agent: q.s.

The liposome composition according to the embodiment of the present invention was produced based on the above-mentioned Examples. It was confirmed that the molar ratio of sulfate ions in the inner water phase to the drug in the entire water phase was 0.36 or more.

InVivoMAb anti-mouse PD-L1 (manufactured by Bio X Cell) was used as the anti-PD-L1 antibody.

The 10 mM histidine/9.4% sucrose solution is a solution in which the concentration of histidine is 10 mM in an aqueous solution containing 9.4 g/100 mL of sucrose. MBT-2 cells were obtained from the JCRB Cell Bank.

(Drug Efficacy Test with Combined use of Anti-PD-L1 Antibody in Tumor-Hearing Model Mouse with Subcutaneous Transplantation of MBT-2)

An anti-PD-L1 antibody (hereinafter, also referred to as PD-L1 Ab) and a topotecan-containing liposome composition according to the embodiment of the present invention (hereinafter, also referred to as Lipo) were used as test substances. For the dilution of PD-L1 Ab, InVivoPure pH 6.5 Dilution Buffer (hereinafter, also referred to as Ab dilution liquid, manufactured by Bio X Cell) was used. For the dilution of Lipo, a 10 mM histidine/9.4% sucrose solution (hereinafter, also referred to as Lipo dilution liquid) was used.

$3 \times 10^6$ MBT-2 cells, which is a mouse bladder cancer cell line, were subcutaneously transplanted into the flank of female C3H/HeN mice to form subcutaneous tumors. Using the tumor volume as an index, the inhibitory effects of PD-L1 Ab alone, Lipo alone, and a combination of PD-L1 Ab and Lipo on subcutaneous tumor growth were evaluated. The PD-L1 Ab and Ab dilution liquid were intraperitoneally administered twice a week for a total of 3 weeks. The Liposome composition according to the embodiment of the present invention and the dilution liquid thereof were administered once a week by tail vein administration for a total of 3 weeks. After the 3-week administration was completed, the drug was discontinued and the tumor volume measurement was continued for 3 weeks.

With regard to a group configuration,

Group 1 was a group to which an Ab dilution liquid and a dilution liquid of the liposome composition according to the embodiment of the present invention were administered, Group 2 was a group to which PD-L1 Ab (10 mg/kg) and a dilution liquid of the liposome composition according to the embodiment of the present invention were administered, Group 3 was a group to which an Ab dilution liquid and the liposome composition (1 mg/kg) according to the embodiment of the present invention were administered, and Group 4 was a group to which PD-L1 Ab (10 mg/kg) and the liposome composition according to the embodiment of the present invention (1 mg/kg) were administered.

Groups 1 to 3 correspond to Comparative Examples, and Group 4 corresponds to Example. The group configuration and dose are shown in Table 3. In Table 3, "Lipo" represents the liposome composition according to the embodiment of the present invention, "Abdomen" represents intraperitoneal administration, "Tail" represents tail vein administration, "Twice/W×3" represents twice a week for a total of 3 weeks, and "Once/W×3" represents once a week for a total of 3 weeks. In addition, changes in tumor volume for each individual in each group are shown in FIGS. 1 to 4.

From the above results, the liposome composition according to the embodiment of the present invention, in a case of being used in combination with PD-L1 Ab, exhibited an excellent growth inhibitory effect with respect to the effect of the liposome composition according to the embodiment of the present invention alone or PD-L1 Ab alone. In addition, it was found that the combined use of the liposome composition according to the embodiment of the present invention with PD-L1 Ab exhibits a significant and unexpected effect that a complete remission state is observed.

(Drug Efficacy Test with Combined Use of Anti-PD-1 Antibody in Tumor-Bearing Model Mouse with Subcutaneous Transplantation of CT26.WT)

InVivoMAb anti-mouse PD-1 (manufactured by Bio X Cell) was used as the anti-PD-1 antibody. The 10 mM histidine/9.4% sucrose solution is a solution prepared such that the concentration of histidine is 10 mM in an aqueous solution containing 9.4 g/100 mL of sucrose. CT26.WT cells were obtained from ATCC.

An anti-PD-1 antibody (hereinafter, also referred to as PD-1 Ab) and the topotecan-containing liposome composition (Lipo) according to the embodiment of the present invention were used as test substances. For the dilution of PD-1 Ab, InVivoPure pH 7.0 Dilution Buffer (hereinafter, also referred to as Ab dilution liquid, manufactured by Bio X Cell) was used. For the dilution of Lipo, a 10 mM histidine/9.4% sucrose solution (hereinafter, also referred to as Lipo dilution liquid) was used.

$1 \times 10^6$ CT26.WT cells, which is a mouse colon cancer cell line, were subcutaneously transplanted into the flank of

TABLE 3

| Group | Test substance | Dose (mg/kg/administration) | | PD-L1 Ab and Ab dilution liquid | | Lipo and Lipo dilution liquid | | Dosage (mL/kg) |
|---|---|---|---|---|---|---|---|---|
| | | PD-L1 Ab | Lipo | Administration route | Administration schedule | Administration route | Administration schedule | |
| 1 | Ab dilution liquid + Lipo dilution liquid | 0 | 0 | Abdomen | Twice/Wx3 | Tail | Once/Wx3 | 10 |
| 2 | PD-L1 Ab + Lipo dilution liquid | 10 | 0 | Abdomen | Twice/Wx3 | Tail | Once/Wx3 | 10 |
| 3 | Ab dilution liquid + Lipo | 0 | 1 | Abdomen | Twice/Wx3 | Tail | Once/Wx3 | 10 |
| 4 | PD-L1 Ab + Lipo | 10 | 1 | Abdomen | Twice/Wx3 | Tail | Once/Wx3 | 10 |

Table 4 shows the number of individuals who maintained a complete remission state in each group until the day of test termination and the complete remission rate (%).

TABLE 4

| Group | Number of individuals remained in complete remission | Number of individuals in group | Complete remission rate (%) |
|---|---|---|---|
| 1 | 0 | 9 | 0 |
| 2 | 1 | 9 | 11.1 |
| 3 | 0 | 9 | 0 |
| 4 | 4 | 9 | 44.4 |

In Group 1 and Group 3, no individual remained in complete remission. In Group 2, 1 out of 9 individuals remained in complete remission. In Group 4, 4 out of 9 individuals remained in complete remission.

female BALB/cerSic mice to form subcutaneous tumors. Treatments with PD-1 Ab alone, Lipo alone, and a combination of PD-1 Ab and Lipo were carried out from post-transplantation day 13, and the effect of prolonging survival time due to the inhibition of subcutaneous tumor growth was evaluated. The PD-1 Ab and Ab dilution liquid were intraperitoneally administered twice a week for a total of 3 weeks. The liposome composition (Lipo) according to the embodiment of the present invention and the dilution liquid thereof were administered once a week by tail vein administration for a total of 3 weeks. After the 3-week administration was completed, the drug was discontinued and the tumor volume measurement was continued for 3 weeks. Mice whose tumor volume exceeded 2,000 mm³ were euthanized from the viewpoint of animal welfare. Survival analysis was carried out by the Kaplan-Meier method, and a significant difference was determined by the Log-Rank test.

With regard to a group configuration,

Group 1 was a group to which an Ab dilution liquid and a Lipo dilution liquid were administered, Group 2 was a group to which PD-1 Ab (10 mg/kg) and a Lipo dilution liquid were administered, Group 3 was a group to which an Ab dilution liquid and the liposome composition (2 mg/kg) according to the embodiment of the present invention were administered, and Group 4 was a group to which PD-1 Ab (10 mg/kg) and the liposome composition (2 mg/kg) according to the embodiment of the present invention were administered.

Figure 5:
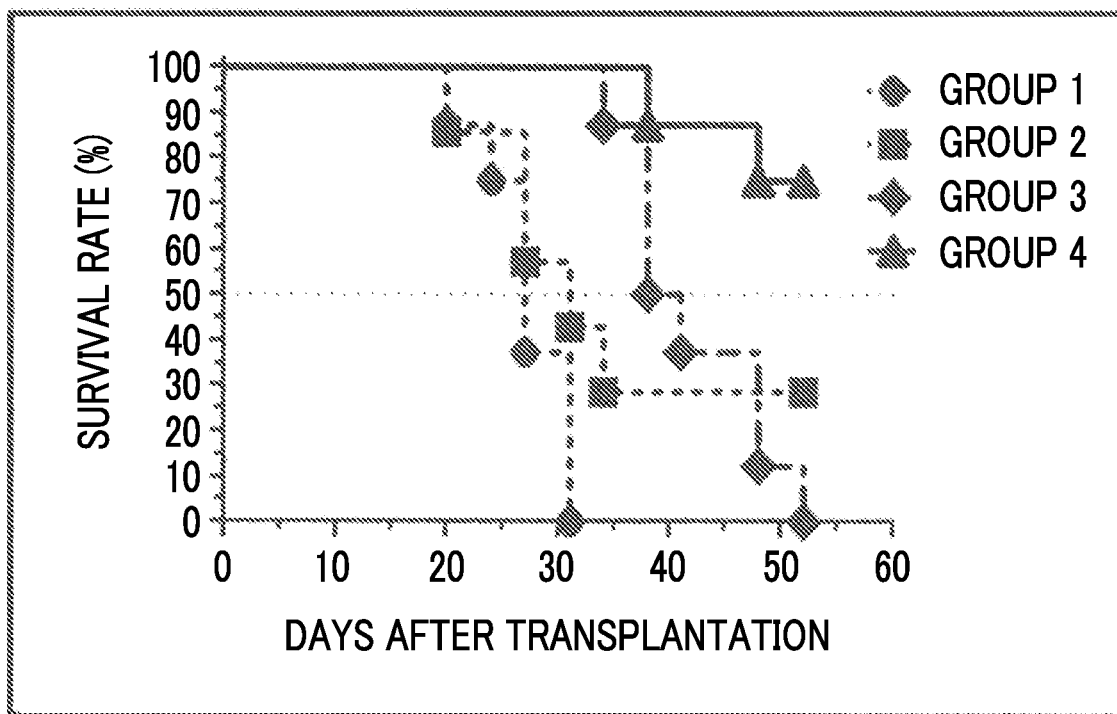
FIG. 5 shows the results of a survival curve in a drug efficacy test with combined use of an anti-PD-1 antibody in a tumor-bearing model mouse with subcutaneous transplantation of CT26.WT.
Figure 6:
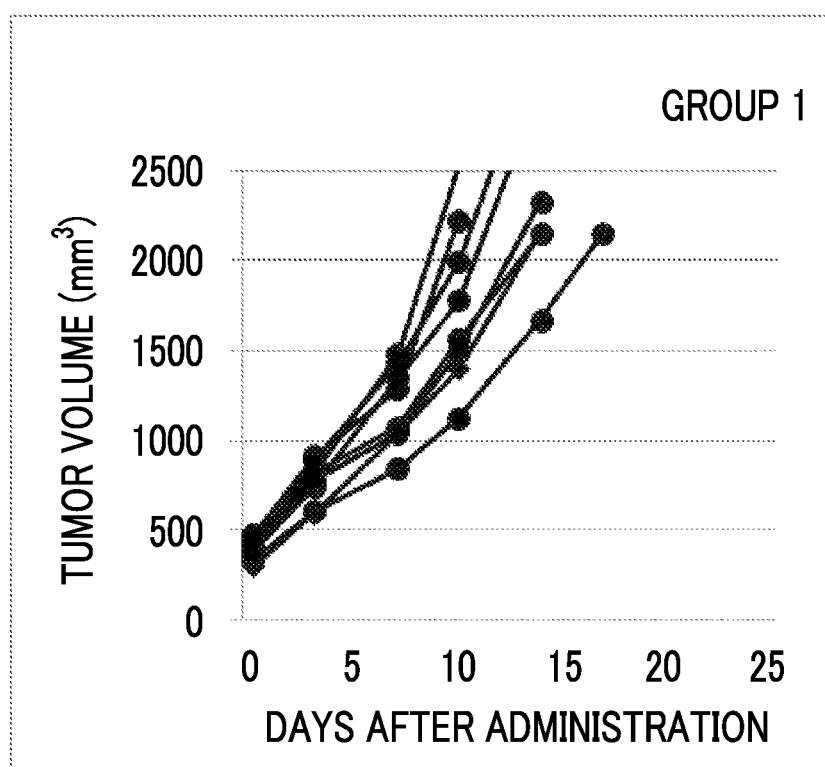
FIG. 6 shows the measurement results of a tumor volume in a drug efficacy test using a tumor-bearing model mouse with subcutaneous transplantation of EMT6.
Figure 7:
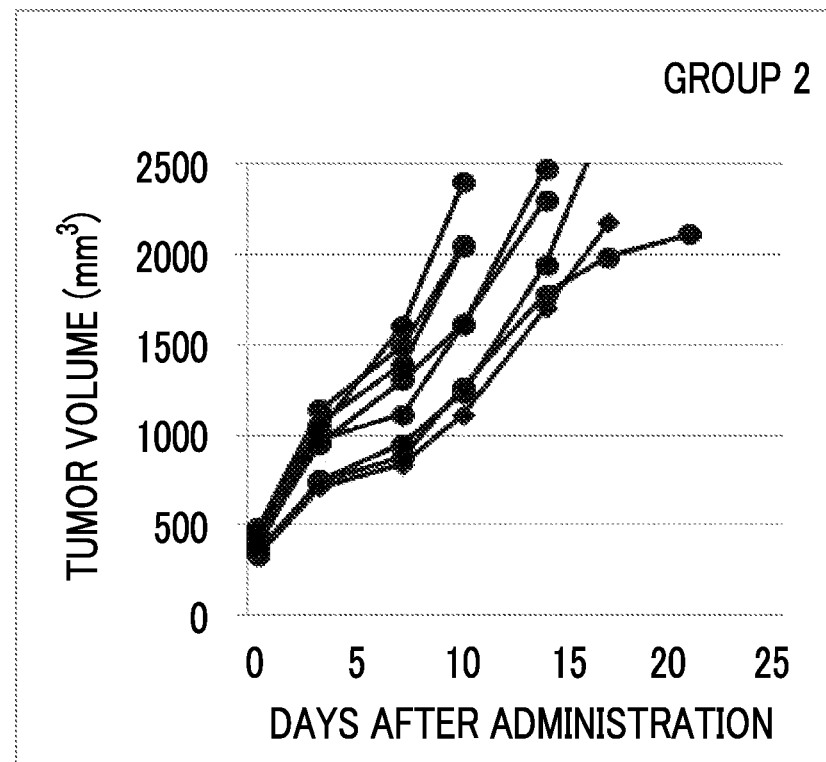
FIG. 7 shows the measurement results of a tumor volume in a drug efficacy test using a tumor-bearing model mouse with subcutaneous transplantation of EMT6.
Figure 8:
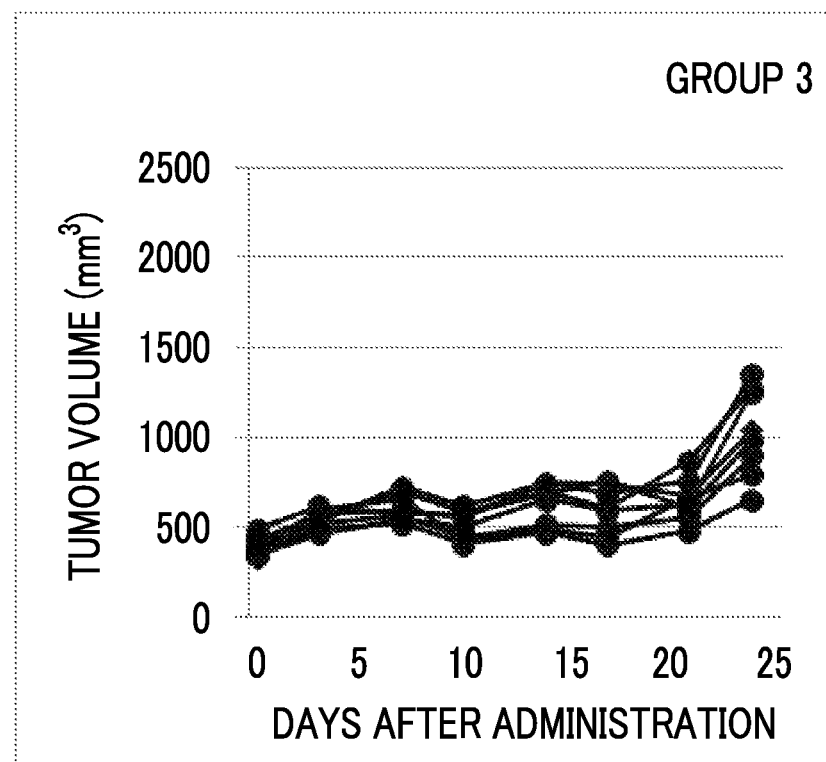
FIG. 8 shows the measurement results of a tumor volume in a drug efficacy test using a tumor-bearing model mouse with subcutaneous transplantation of EMT6.
Figure 9:
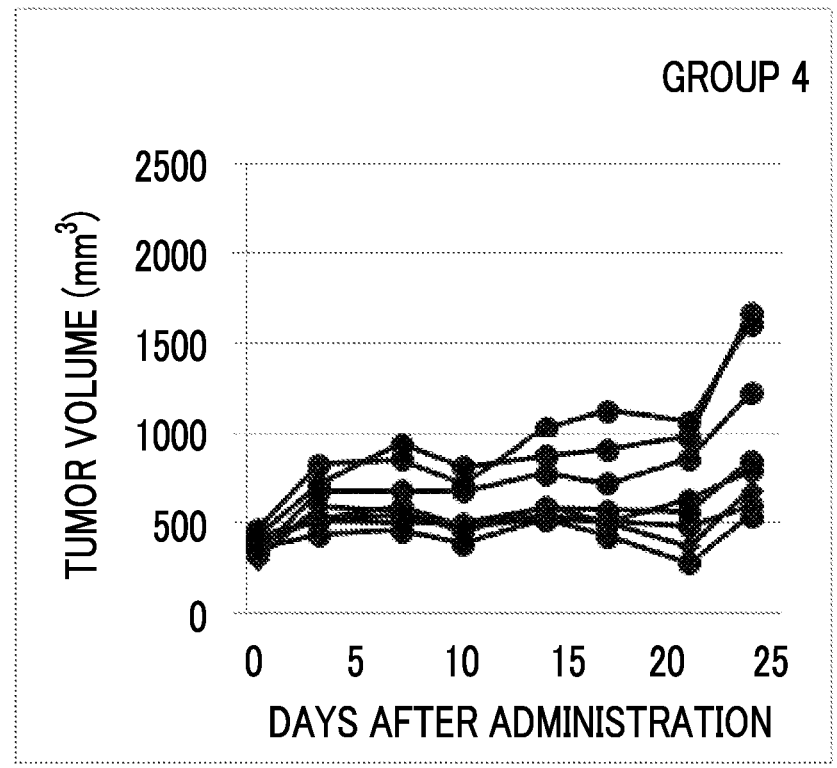
FIG. 9 shows the measurement results of a tumor volume in a drug efficacy test using a tumor-bearing model mouse with subcutaneous transplantation of EMT6.

Groups 1 to 3 correspond to Comparative Examples, and Group 4 corresponds to Example. The group configuration and dose are shown in Table 5. In Table 5, "Lipo" represents the liposome composition according to the embodiment of the present invention, "Abdomen" represents intraperitoneal administration, "Tail" represents tail vein administration, "Twice/W×3" represents twice a week for a total of 3 weeks, and "Once/W×3" represents once a week for a total of 3 weeks. In addition, the survival curve of each group is shown in FIG. 5.

Group 4 exhibited a statistically significant effect of prolonging the survival time with respect to each of Groups 1 to 3 which are Comparative Examples, and 75% of the individuals survived on the day of test termination.

From the above results, it is clear that the liposome composition according to the embodiment of the present invention, in a case of being used in combination with PD-1 Ab, exhibits an excellent survival prolonging effect with respect to the effect of the liposome composition according to the embodiment of the present invention alone or PD-1 Ab alone.

(Drug Efficacy Test with Combined Use of anti-CTLA-4 Antibody in EMT6 Model Mouse)

InVivoMAb anti-mouse CTLA-4 (manufactured by Bio X Cell) was used as the anti-CTLA-4 antibody.

An anti-CTLA-4 antibody (hereinafter, also referred to as CTLA-4 Ab) and the topotecan-containing liposome composition (Lipo) according to the embodiment of the present invention were used as test substances. For the dilution of CTLA-4 Ab, InVivoPure pH 7.0 Dilution Buffer (hereinafter, also referred to as Ab dilution liquid, manufactured by Bio X Cell) was used. For the dilution of Lipo, a 5% sugar solution (hereinafter, also referred to as Lipo dilution liquid, manufactured by Otsuka Pharmaceutical Factory, Inc.) was used.

$2.25 \times 10^6$ EMT6 cells, which is a mouse breast cancer cell line, were subcutaneously transplanted into the flank of female Balb/c mice to form subcutaneous tumors. Using the tumor volume as an index, the inhibitory effects of CTLA-4 Ab alone, Lipo alone, and a combination of CTLA-4 Ab and Lipo on subcutaneous tumor growth were evaluated. The CTLA-4 Ab and Ab dilution liquid were intraperitoneally administered twice a week for a total of 3 weeks. The liposome composition according to the embodiment of the present invention and the dilution liquid thereof were administered once a week by tail vein administration for a total of 3 weeks. After the 3-week administration was completed, the drug was discontinued and the tumor volume measurement was continued.

With regard to a group configuration,

Group 1 was a group to which an Ab dilution liquid and a dilution liquid of the liposome composition according to the embodiment of the present invention were administered, Group 2 was a group to which CTLA-4 Ab (10 mg/kg) and a dilution liquid of the liposome composition according to the embodiment of the present invention were administered,

TABLE 5

| Group | Test substance | Dose (mg/kg/administration) PD-1 Ab | Dose (mg/kg/administration) Lipo | PD-1 Ab and Ab dilution liquid Administration route | PD-1 Ab and Ab dilution liquid Administration schedule | Lipo and Lipo dilution liquid Administration route | Lipo and Lipo dilution liquid Administration schedule | Dosage (mL/kg) |
|---|---|---|---|---|---|---|---|---|
| 1 | Ab dilution liquid + Lipo dilution liquid | 0 | 0 | Abdomen | Twice/W×3 | Tail | Once/W×3 | 10 |
| 2 | PD-1 Ab + Lipo dilution liquid | 10 | 0 | Abdomen | Twice/W×3 | Tail | Once/W×3 | 10 |
| 3 | Ab dilution liquid + Lipo | 0 | 2 | Abdomen | Twice/W×3 | Tail | Once/W×3 | 10 |
| 4 | PD-1 Ab + Lipo | 10 | 2 | Abdomen | Twice/W×3 | Tail | Once/W×3 | 10 |

Table 6 shows the median survival time calculated from the time of transplantation in each group, and the survival rate (%) on the day of test termination, and Table 7 shows the results of the Log-Rank test. In a case where a p-value was less than 0.05, it was determined that there was a statistically significant difference.

TABLE 6

| Group | Median survival time | Survival rate on date of termination |
|---|---|---|
| 1 | 27 | 0% |
| 2 | 31 | 28.6% |
| 3 | 39.5 | 0% |
| 4 | ND > 52 | 75% |

TABLE 7

| Comparative group | p value | Significant difference |
|---|---|---|
| 1 vs 2 | p = 0.1227 | No significant difference |
| 1 vs 3 | p = 0.0001 | Significant difference |
| 1 vs 4 | p = 0.0001 | Significant difference |
| 2 vs 3 | p = 0.8334 | No significant difference |
| 2 vs 4 | p = 0.0281 | Significant difference |
| 3 vs 4 | p = 0.0020 | Significant difference |

Group 3 was a group to which an Ab dilution liquid and the liposome composition (4 mg/kg) according to the embodiment of the present invention were administered, and Group 4 was a group to which CTLA-4 Ab (10 mg/kg) and the liposome composition (4 mg/kg) according to the embodiment of the present invention were administered.

Groups 1 to 3 correspond to Comparative Examples, and Group 4 corresponds to Example. The group configuration and dose are shown in Table 8. In Table 8, "Lipo" represents the liposome composition according to the embodiment of the present invention, "Abdomen" represents intraperitoneal administration, "Tail" represents tail vein administration, "Twice/W×3" represents twice a week for a total of 3 weeks, and "Once/W×3" represents once a week for a total of 3 weeks. In addition, changes in tumor volume for each individual in each group are shown in FIGS. 6 to 9.

TABLE 8

| | | Dose (mg/kg/administration) | | CTLA-4 Ab and Ab dilution liquid | | Lipo and Lipo dilution liquid | | |
|---|---|---|---|---|---|---|---|---|
| Group | Test substance | CTLA-4 Ab | Lipo | Administration route | Administration schedule | Administration route | Administration schedule | Dosage (mL/kg) |
| 1 | Ab dilution liquid + Lipo dilution liquid | 0 | 0 | Abdomen | Twice/Wx3 | Tail | Once/Wx3 | 10 |
| 2 | CTLA-4 Ab + Lipo dilution liquid | 10 | 0 | Abdomen | Twice/Wx3 | Tail | Once/Wx3 | 10 |
| 3 | Ab dilution liquid + Lipo | 0 | 4 | Abdomen | Twice/Wx3 | Tail | Once/Wx3 | 10 |
| 4 | CTLA-4 Ab + Lipo | 10 | 4 | Abdomen | Twice/Wx3 | Tail | Once/Wx3 | 10 |

From the above results, it was shown that the pharmaceutical formulation according to the embodiment of the present invention is very useful for preventing or treating cancer and has an unexpected tumor growth inhibitory effect.

In particular, it has become possible to provide a new pharmaceutical formulation by administering a liposome composition including topotecan in combination with at least one antibody that inhibits PD-1, PD-L1, and CTLA-4 as an immune checkpoint inhibitor.

The pharmaceutical formulation according to the embodiment of the present invention is useful as a pharmaceutical formulation for preventing or treating cancer. The administration method according to the embodiment of the present invention is useful as a method for administering a pharmaceutical formulation for preventing or treating cancer. Furthermore, the treatment method according to the embodiment of the present invention is useful as a treatment method for preventing or treating cancer.

What is claimed is:

1. A pharmaceutical formulation consisting of:
   (A) a liposome composition in combination with (B) an immune checkpoint inhibitor which is not contained in the liposome composition,
   wherein the liposome composition includes, as constitutional components of a liposome membrane, a hydrophilic polymer-modified diacylphosphatidylethanolamine; a dihydrosphingomyelin; and cholesterols; the liposome composition includes a drug consisting of topotecan or a salt thereof and has an inner water phase containing ammonium sulfate, a molar ratio of sulfate ions in the inner water phase to the drug in an entire water phase is 0.36 or more, and the liposome composition and the immune checkpoint inhibitor are administered simultaneously or sequentially.

2. The pharmaceutical formulation according to claim 1, wherein the molar ratio of sulfate ions in the inner water phase to the drug in the entire water phase is 0.6 or more and 1.8 or less.

3. The pharmaceutical formulation according to claim 1, wherein the hydrophilic polymer-modified diacylphosphatidylethanolamine is a polyethylene glycol- or methoxy polyethylene glycol-modified diacylphosphatidylethanolamine.

4. The pharmaceutical formulation according to claim 1, wherein a percentage of the hydrophilic polymer-modified diacylphosphatidylethanolamine in the constitutional components of the liposome membrane is 2 to 10 mol %.

5. The pharmaceutical formulation according to claim 1, wherein a percentage of cholesterols in the constitutional components of the liposome membrane is 35 to 43 mol %.

6. The pharmaceutical formulation according to claim 1, wherein a particle size is 150 nm or less.

7. The pharmaceutical formulation according to claim 1, wherein an outer water phase has a pH of 5.5 to 8.5.

8. The pharmaceutical formulation according to claim 1, wherein the dihydrosphingomyelin is a dihydrosphingomyelin containing a long-chain alkyl group having 16 carbon atoms and a long-chain alkyl group having 18 carbon atoms.

9. The pharmaceutical formulation according to claim 1, wherein a drug release rate from a liposome in plasma having an ammonium concentration of 1 mmol/L or less is 20%/24 hours or less at 37° C., and a drug release rate from a liposome in plasma having an ammonium concentration of 4 to 6 mmol/L is 60%/24 hours or more at 37° C.

10. The pharmaceutical formulation according to claim 1, wherein the immune checkpoint inhibitor includes at least one selected from a PD-1 inhibitor, a PD-L1 inhibitor, a PD-L2 inhibitor, or a CTLA-4 inhibitor.

11. The pharmaceutical formulation according to claim 10,
wherein the immune checkpoint inhibitor includes at least one selected from a PD-1 inhibitor, a PD-L1 inhibitor, or a CTLA-4 inhibitor.

12. The pharmaceutical formulation according to claim 1,
wherein the administration is carried out at a dose and for a dosing period that exhibit a therapeutic synergistic effect.

13. The pharmaceutical formulation according to claim 1,
wherein a subject of administration has resistance to topotecan.

14. A method for treating a disease of a subject, the method comprising:
administering (A) a liposome composition in combination with (B) an immune checkpoint inhibitor which is not contained in the liposome composition to a subject simultaneously or sequentially at an effective dose and for an effective dosing period exhibiting a therapeutic synergistic effect,
in which the liposome composition includes, as constitutional components of a liposome membrane, a hydrophilic polymer-modified diacylphosphatidylethanolamine; a dihydrosphingomyelin; and cholesterols, the liposome composition includes a drug consisting of topotecan or a salt thereof and has an inner water phase containing ammonium sulfate, and a molar ratio of sulfate ions in the inner water phase to the drug in an entire water phase is 0.36 or more.

15. The method according to claim 14, wherein the disease is cancer.

16. A pharmaceutical formulation consisting essentially of:
(A) a liposome composition in combination with (B) an immune checkpoint inhibitor which is not contained in the liposome composition,
wherein the liposome composition includes, as constitutional components of a liposome membrane, a hydrophilic polymer-modified diacylphosphatidylethanolamine; a dihydrosphingomyelin; and cholesterols, the liposome composition includes a drug consisting of topotecan or a salt thereof and has an inner water phase containing ammonium sulfate, a molar ratio of sulfate ions in the inner water phase to the drug in an entire water phase is 0.36 or more, and the liposome composition and the immune checkpoint inhibitor are administered simultaneously or sequentially.

* * * * *